(12) United States Patent
Walker et al.

(10) Patent No.: US 9,827,115 B2
(45) Date of Patent: Nov. 28, 2017

(54) INSTRUMENTED LINKAGE SYSTEM

(75) Inventors: Peter S. Walker, New York, NY (US);
Rachel E. Forman, Astoria, NY (US);
Chih-Shing Wei, Lattingtown, NY (US)

(73) Assignee: ZIMMER INC., Warsaw (*) Notice: Subject to any disclaimer, the term of this patent is extended or adjusted under 35 U.S.C. 154(b) by 1541 days.

(21) Appl. No.: 12/514,870

(22) PCT Filed: Jan. 25, 2008

(86) PCT No.: PCT/US2008/052030
§ 371 (c)(1),
(2), (4) Date: Mar. 10, 2010

(87) PCT Pub. No.: WO2008/118524
PCT Pub. Date: Oct. 2, 2008

(65) Prior Publication Data
US 2010/0174287 A1 Jul. 8, 2010

Related U.S. Application Data

(60) Provisional application No. 60/897,809, filed on Jan. 26, 2007.

(51) Int. Cl.
*A61F 5/00* (2006.01)
*A61F 2/46* (2006.01)
(Continued)

(52) U.S. Cl.
CPC ............ *A61F 2/4657* (2013.01); *A61B 90/36* (2016.02); *A61B 90/50* (2016.02); *A61B 17/154* (2013.01); *A61B 34/20* (2016.02); *A61B 2034/107* (2016.02); *A61B 2034/2068* (2016.02); *A61B 2034/252* (2016.02); *A61B 2090/061* (2016.02); *A61B 2090/067* (2016.02); *A61F 2002/4632* (2013.01); *A61F 2002/4658* (2013.01); *A61F 2002/4668* (2013.01)

(58) Field of Classification Search
CPC ..... A61B 17/15; A61B 17/155; A61B 17/157; A61B 90/36; A61B 90/50
USPC .................. 606/87, 88, 96, 97, 98
See application file for complete search history.

(56) References Cited

U.S. PATENT DOCUMENTS 5,748,767 A 5/1998 Raab
6,033,415 A 3/2000 Mittelstadt et al.
(Continued)

FOREIGN PATENT DOCUMENTS

WO WO00/35366 A1 6/2000
WO WO2005/122916 A1 12/2005

OTHER PUBLICATIONS

Product description—Zimmer MIS Multi-Reference® 4-in-1 Femoral Instrumentation 2008 @ http://www.zimmer.com/z/ctl/op/global/action/1/id/50/template/MP/prcat/M3/prod/y1/11/2008.
(Continued)

*Primary Examiner* — David Isabella
*Assistant Examiner* — Christine Nelson
(74) *Attorney, Agent, or Firm* — Norton Rose Fulbright Canada LLP

(57) ABSTRACT

An instrumented linkage system (100) to facilitate accuracy and efficiency of a surgical procedure is disclosed. The linkage system may be directly attached to a bone and used to register the bone to a computer. The linkage system may also be used to verify the accuracy and alignment of planned resections relative to the bone.

7 Claims, 28 Drawing Sheets

(51) Int. Cl.
    *A61B 90/00* (2016.01)
    *A61B 90/50* (2016.01)
    *A61B 17/15* (2006.01)
    *A61B 34/20* (2016.01)
    *A61B 34/10* (2016.01)
    *A61B 34/00* (2016.01)

(56) References Cited

U.S. PATENT DOCUMENTS

| | | | |
|---|---|---|---|
| 6,071,288 | A | 6/2000 | Carol et al. |
| 7,104,998 | B2 | 9/2006 | Yoon et al. |
| 2004/0246469 | A1 | 12/2004 | Hirose |
| 2006/0217737 | A1 | 9/2006 | Iversen |
| 2007/0156157 | A1 | 7/2007 | Nahum et al. |

OTHER PUBLICATIONS

Walker, Peter S., et al., "Feasibility of Navigated Freehand Cutting in Total Knee Surgery," The Journal of Anthropology—2006.

Kinzel, G. L et al., Measurement of the Total Motion Between Two Body Segments—I. Analytical Development, II. Description of Application, Biomechanics, 1972, vol. 5, pp. 93-105 and pp. 283-293 Pergamon Press, Great Britain.

Kirstukas, S.J., et al., 6R Instrumented Spatial Linkages for Anatomical Joint Motion Measurement—Part 2: Calibration, Biomechanical Engineering, 1992, vol. 114, pp. 101-110, ASME.

Liu, W. And Panjabi, M., Technical Note: "On Improving the Accuracy of Instrumented Spatial Linkage System," Biomechanics, 1996, vol. 29, No. 10, pp. 1383-1385, Pergamon Press, Great Britain.

Sholukha, V., et al., Technical Note: "Calibration and validation of 6 DOFs instrumental spatial linkage for biomechanical applications. A practical approach." Medical Engineering & Physics, 26 (2004) 251-260.

Walker, Peter S. et al., "Development and Evaluation of an Instrumented Linkage System for Total Knee Surgery," Clinical Orthopaedics and Related Research No. 463, pp. 68-73, 2007 Lippincott Williams & Wilkins.

Balicki, M. et al., "Novel Navigation Technique for Jig Placement in Total Knee Replacement Using an Instrumented Linkage," Transactions, vol. 31, Chicago, IL 2006.

Forman, R. et al., Biomechanical Analysis of the Reverse Total Shoulder, Transactions, vol. 32, San Diego, CA 2007.

Hoffart, E. H., "Computer-Navigation in Total Knee Replacement with the TC-Plus (TM) Solution Knee System Method Evaluation First Results," The Journal of Bone and Joint Surgery, British vol. 86-B, Issue SUPP_IV, 407.

MicroScribe® for Medical, @ http://www.imersion.com/digitzer/products/microscribe_for_medical.php.

Krakow, K.A., MD, et al., "A New Technique for Determining Proper Mechanical Axis Alignment During Total Knee Arthroplasty: Progress Toward Computer-Assisted TKA," Orthopedics; Jul. 1999; vol. 22, No. 7; ProQuest Nursing & Allied Health Service.

Siston, Robert A., et al., "Evaluation of a new algorithm to determine the hip joint center," Journal of Biomechanics, 39 (2006) pp. 125-130.

McCarthy, J.M., Introduction to Theoretical Kinematics, The MIT Press, Cambridge, Massachusetts, London, England.

International Preliminary Report on Patentability dated Jul. 28, 2009, in related International Patent Application No. PCT/US2008/052030.

Article "Praxiteles: a miniature bone-mounted robot for minimal access total knee arthroplasty", Plaskos et al., Int. J. Medical Robotics and Computer Assisted Surgery 2005, pp. 67-79.

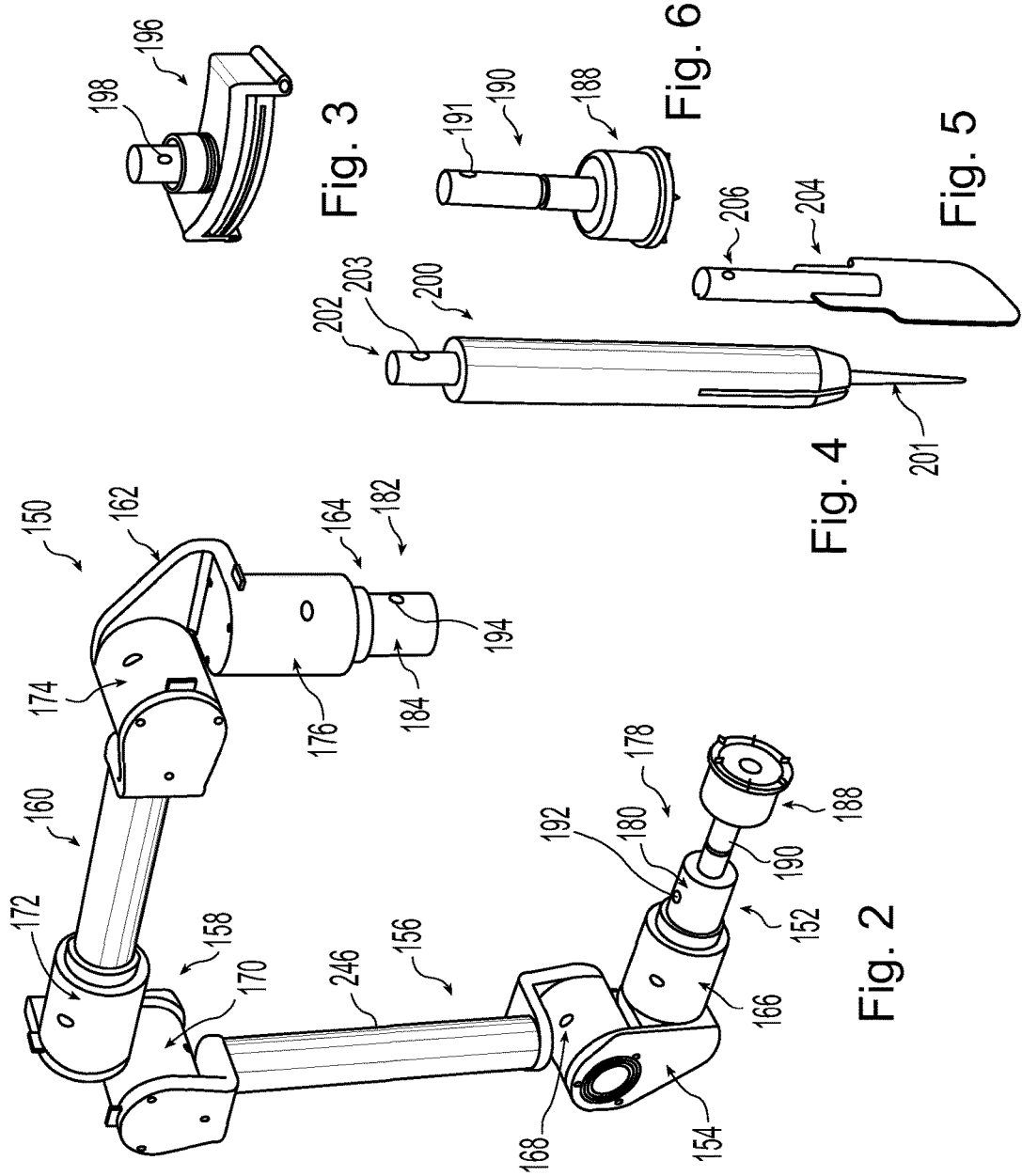

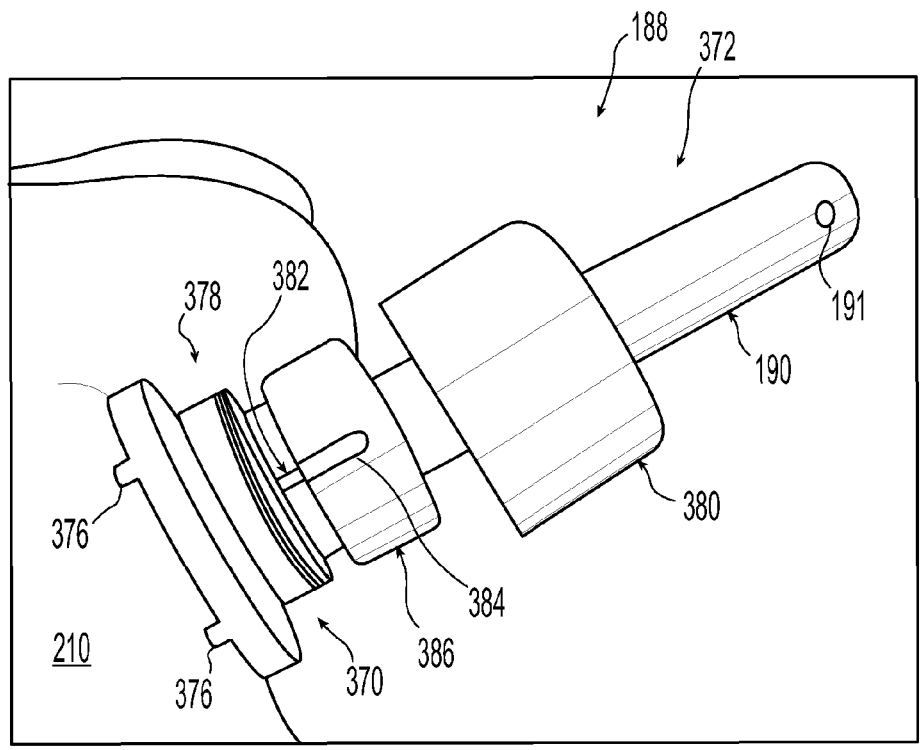
Fig. 17
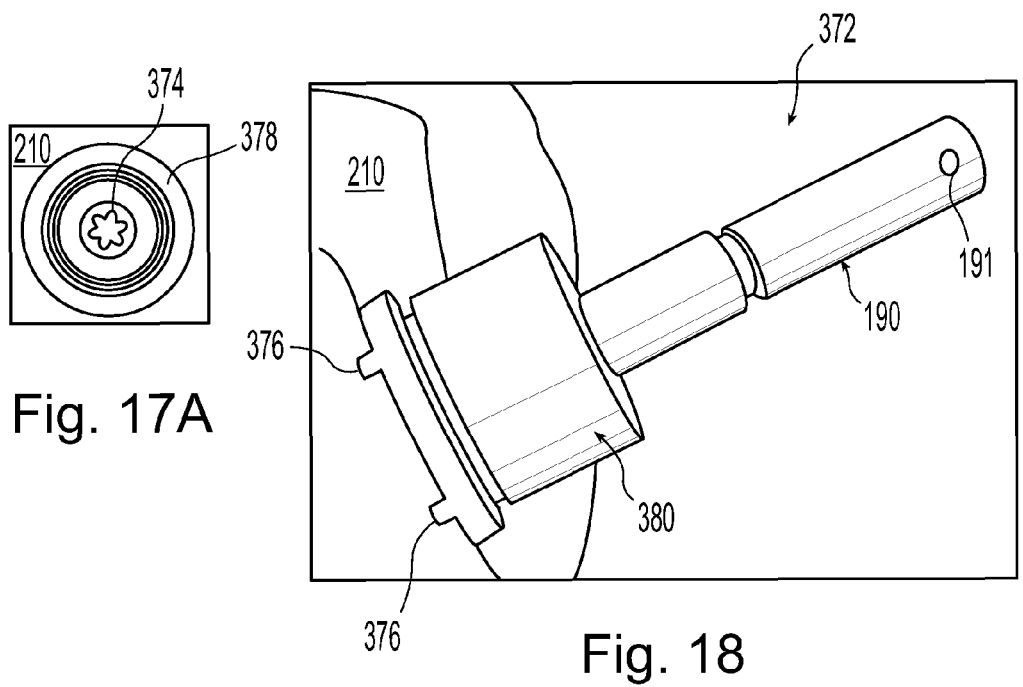
Fig. 17A
Fig. 18

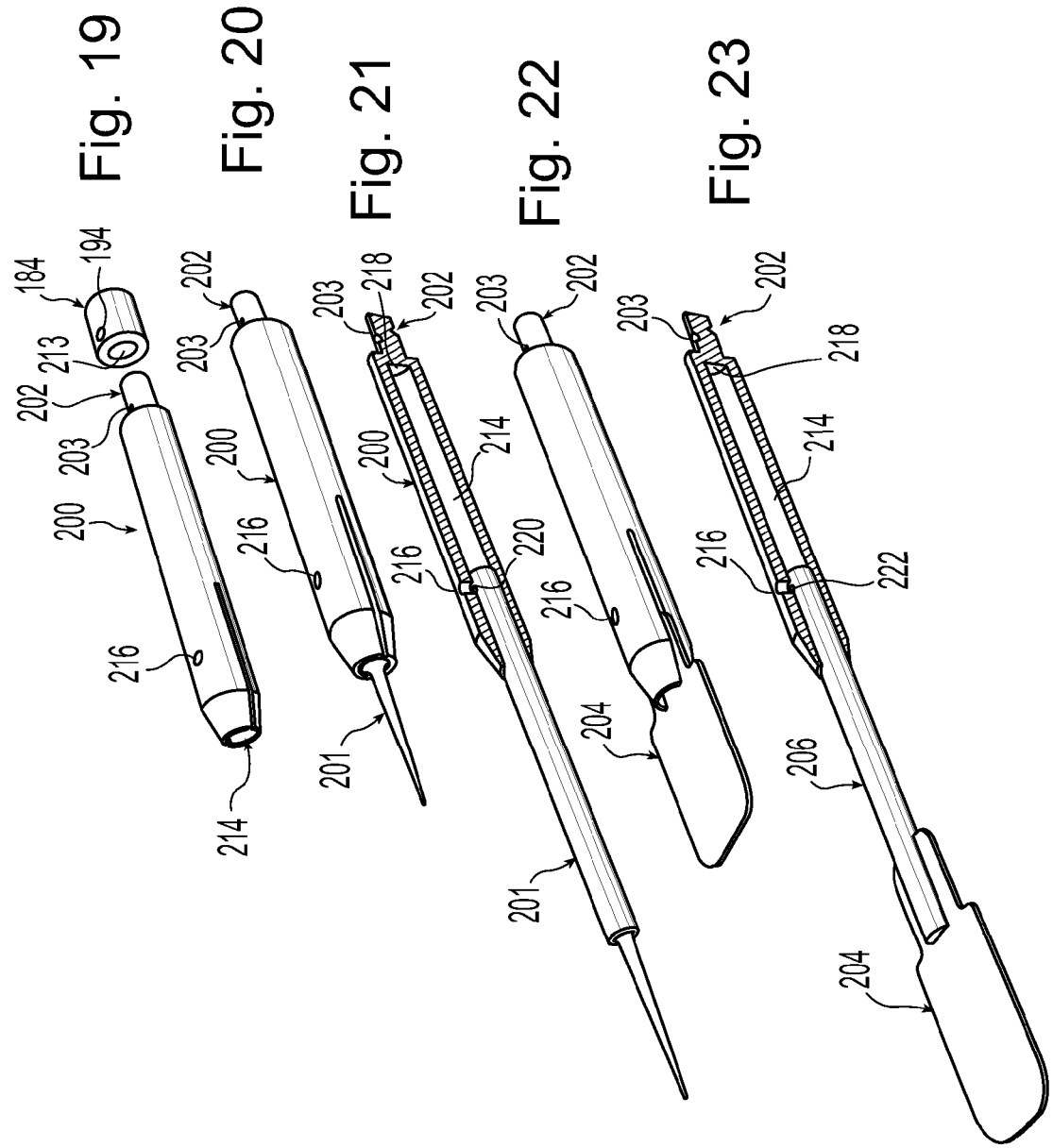

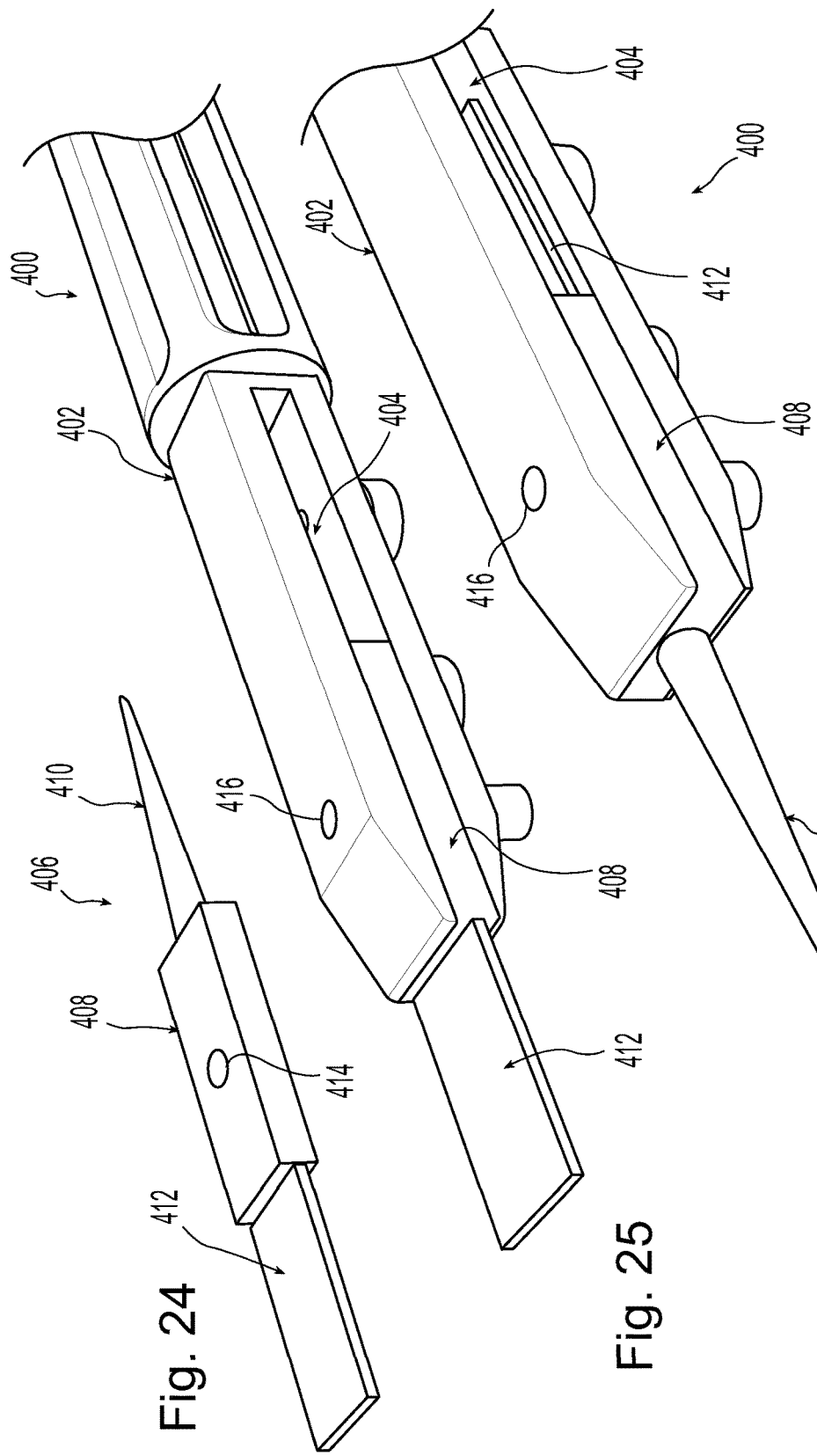

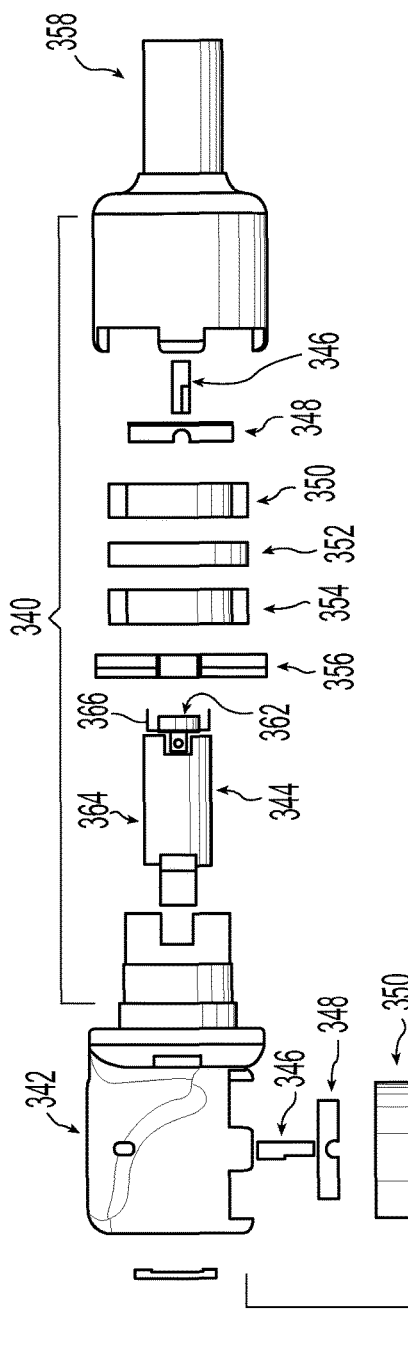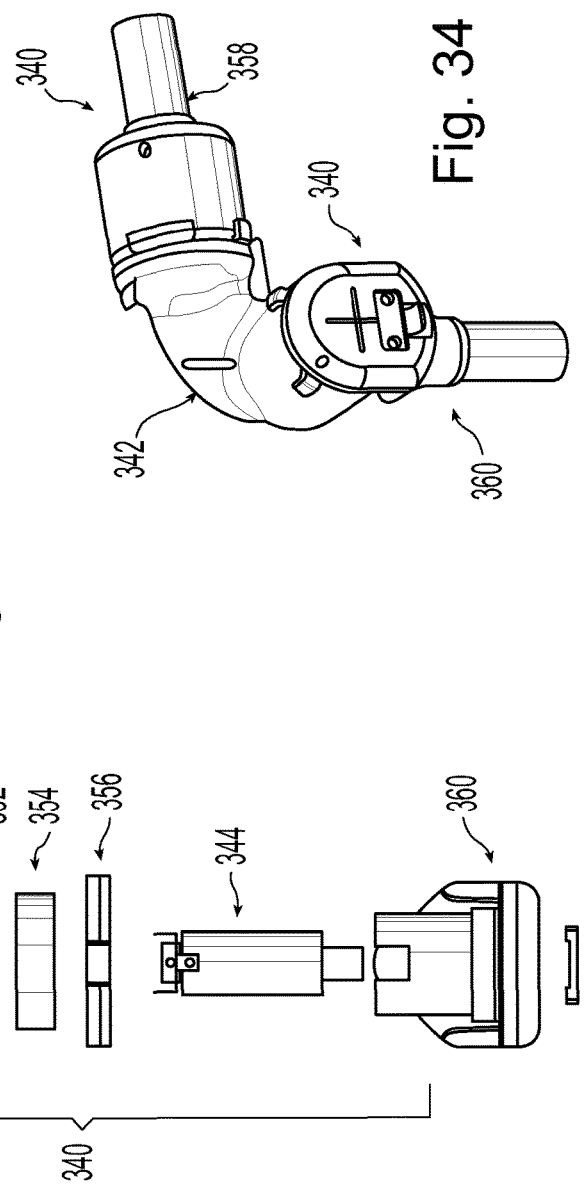

INSTRUMENTED LINKAGE SYSTEM

CROSS REFERENCE TO RELATED APPLICATIONS

This application claims the benefit of U.S. Provisional Application Ser. No. 60/897,809, filed Jan. 26, 2007, titled INSTRUMENTED LINKAGE SYSTEM, the disclosure of which is expressly incorporated by reference herein.

FIELD OF THE INVENTION

The present disclosure relates to an instrumented linkage system and methods of using the same. More particularly, the present disclosure relates to an instrumented linkage system attachable directly to a bone to provide enhanced accuracy and efficiency for an orthopedic surgery.

BACKGROUND AND SUMMARY OF THE INVENTION

The overall goals of total knee surgery are to implant the components at the required alignments based on defined landmarks and axes, and to achieve the optimal balance of the surrounding soft tissues for the full range of flexion, the purpose being to achieve the best possible durability and function. For example, if the frontal plane alignment results in under-corrected varus, the forces on the medial side can be excessive causing premature wear and loosening. In the sagittal plane, too much extension in the placement of the femoral component relative to the femur can lead to anterior notching and fracture, or a reduction of flexion. Rotational inaccuracy of the tibial component can lead to binding and wear, and patella subluxation.

In general, it has been found that the use of navigation systems has resulted in improved alignments by a reduction of outliers, compared with mechanical alignment systems. This is probably due to the greater consistency of determining the bony landmarks and the definition of the femoral axis using the mechanical axis to the center of the femoral head, rather than the uncertainty of the anatomic axis using present intramedullary rod instruments. Navigation systems include optical tracking systems and electromagnetic tracking systems.

At the ligament balancing stage, navigation used to measure the varus and valgus deviations at different flexion angles has allowed for a more consistent result rather than using blocks with manual non-measured methods. However all systems, whether navigation or mechanical, require the correct definition of the landmarks and axes, and even then errors can occur during the bone cutting procedure itself. An advantage of navigation in this regard is that cuts can be quantitatively checked and corrected if necessary. A limitation of navigation in ligament balancing is that the varus and valgus deviations, while measured accurately, are applied manually with unknown forces. In practical terms, while having many advantages, present navigation systems are expensive, require set-up and skilled maintenance and operation, and add to the operating time.

An alternate measurement system for all steps of the procedure is the use of an instrumented linkage. The mathematical principles for using a succession of links joined by instrumented revolute joints for measuring the coordinate and orientation of the end link relative to the first have been well established (Kinzel et al, 1972; McCarthy, 1990). The application of such spatial linkages to measure joint motions was described, as well as techniques for design configuration and calibration to optimize accuracy (Kirstukas et al, 1992a, 1992b). One example of using calibration procedures showed that accuracies better than 0.2 mm and 0.2 degree could be achieved (Liu and Panjabi, 1996). In a design adapted for biomechanical applications, 1 mm and 1 degree accuracy were obtained (Sholukha et al, 2004).

Instrumented linkages available commercially (Faro Arm; Microscribe) are primarily used for on-site inspection and quality control of engineered parts and assemblies, and for reverse engineering. The Microscribe is however being applied to orthotics and prosthetics fitting, stereotactic registrations, 3-D imaging and MIS surgery, and other procedures.

The present disclosure relates to an instrumented linkage system. The instrumented linkage system may be used in various medical operations, including trauma and surgeries. An exemplary surgical operation is a total knee replacement surgery. Another exemplary surgical operation is a hip replacement surgery. An exemplary trauma operation is locating screws for coupling to an intramedullary rod.

In an exemplary embodiment, the instrumented linkage system is directly attached to an anatomical structure, such as a bone, for example, of a patient. The system may use a digitizing fixture, such as a pointer, to register the anatomical structure with a computer. A cutting guide is then attached to the anatomical structure. The system may then use a paddle inserted in the cut slot of the cutting guide to verify the correct orientation and location of the slot defined by the slotted cutting guide.

In another exemplary embodiment of the present disclosure, a method of placing a cutting guide on at least one bone is provided. The method comprising the steps of affixing a first end of an instrumented linkage system to a substrate; coupling a digitizing fixture to a second end of said instrumented linkage system; digitizing a plurality of points of said at least one bone; locating said cutting guide with said instrumented linkage system; and securing said cutting guide to said at least one bone. In one example, said substrate is a first bone. In another example, said step of affixing a first end of an instrumented linkage system to a substrate includes the steps of coupling a first member of a bone mount to said first bone with a fastener; coupling a second member of said bone mount to said first member of said bone mount; and coupling said second member of said bone mount to said instrumented linkage system. In a further example, said substrate is a patient support and said step of affixing a first end of an instrumented linkage system to a substrate includes the steps of coupling a patient support mount to said substrate; and coupling said instrumented linkage system to said patient support mount. In another example, said step of digitizing a plurality of points of said at least one bone includes the steps of prompting for a first landmark point; receiving an indication that a tip of said digitizing fixture is positioned at said first landmark point; and receiving an indication of a position of each of a plurality of moveable couplings of said instrumented linkage system. In still another example, said step of securing said cutting guide to said at least one bone includes the steps of affixing a frame of said cutting guide to said at least one bone; coupling a paddle fixture to said instrumented linkage system; placing an end of said paddle fixture into a guide member of said cutting guide; adjusting an angular orientation of said guide member relative to said frame based on a determined location of said end of said paddle fixture. In a further example thereof, said step of securing said cutting guide to said at least one bone further includes the steps of locking said angular orientation of said guide member relative to said frame; adjusting a translational position of said guide member relative to said frame based on said determined location of said end of said paddle fixture; and locking said translational position of said guide member relative to said frame.

In another exemplary embodiment of the present disclosure, a method of digitizing a bone is provided. The method comprising the steps of affixing a first end of an instrumented linkage system to said bone; coupling a digitizing fixture to a second end of said instrumented linkage system; providing an indication of when a tip of said digitizing fixture is contacting a first point on said bone; receiving an indication of a position of each of a plurality of moveable couplings of said instrumented linkage system when said tip of said digitizing fixture is contacting a first point on said bone. In one example, said first point is a first landmark point and the method further comprises the step of providing a prompt for said first landmark point so that said tip of said digitizing fixture is contacting a first landmark point on said bone.

In a further exemplary embodiment of the present disclosure, a method of determining a relative motion between a first bone and a second bone. The method comprising the steps of providing an instrumented linkage system, said instrumented linkage system being a passive system; affixing a first end of said instrumented linkage system to a first known location on said first bone; affixing a second end of said instrumented linkage system to a second known location on said second bone; and monitoring a position of each of a plurality of moveable couplings of said instrumented linkage system. In one example, said first bone and said second bone are part of a joint and by monitoring said position of each of said plurality of moveable coupling of said instrumented linkage system a separation of said joint may be determined. In another example, said first known location on said first bone is determined by the steps of: affixing said first end of said instrumented linkage system to said first bone; coupling a digitizing fixture to said second end of said instrumented linkage system; providing for each of a plurality of landmark points an indication of when a tip of said digitizing fixture is contacting a respective landmark point on said first bone; for each respective landmark point, receiving an indication of a position of each of a plurality of moveable couplings of said instrumented linkage system when said tip of said digitizing fixture is contacting said respective landmark point on said first bone; and determining said first known location based on said received indications of said positions of said plurality of moveable couplings. In a further example, said second known location on said second bone is determined by the steps of: affixing said second end of said instrumented linkage system to said second bone; coupling a digitizing fixture to said first end of said instrumented linkage system; and providing for each of a plurality of landmark points an indication of when a tip of said digitizing fixture is contacting a respective landmark point on said second bone; for each respective landmark point, receiving an indication of a position of each of a plurality of moveable couplings of said instrumented linkage system when said tip of said digitizing fixture is contacting said respective landmark point on said second bone; and determining said second known location based on said received indications of said positions of said plurality of moveable couplings.

In still another exemplary embodiment of the present disclosure, an instrumented linkage system for attachment to at least one bone is provided. The system comprising a passive link system including a plurality of links connected together through a plurality of moveable couplings; a first bone mount coupled to a first end of said passive link system; a plurality of separate fixtures each attachable to a second end of said passive link system. Said plurality of separate fixtures including at least two of a second bone mount; a pointer for digitization of said first bone; a saw; and a paddle for accurate placement of at least one cutting guide on said first bone. The system further comprising a processing system operatively coupled to said plurality of moveable couplings to receive indications of a position of each of said plurality of moveable couplings. In one example, said processing system includes an output device which prompts for one of said plurality of fixtures to attach to said second end of said passive link system. In another example, said output device is a display. In still another example, said display provides an indication of said current position of said second end of said passive link system and a target position of said second end of said passive link system. In yet still another example, said display provides an indication of said current orientation of said second end of said passive link system and a target orientation of said second end of said passive link system. In a further example, said output device is supported by said passive link system.

In yet a further exemplary embodiment of the present disclosure, an instrumented linkage system is provided. The system including an arm with a plurality of degrees of freedom and an attachment boss at each end of said arm. Said attachment boss adapted to attach to separate fixtures. Said fixtures including an attachment device for rigid connection to a bone. Said fixtures including a pointer for digitization. Said fixtures including a drill guide for placing of a hole in a bone. Said fixtures including a paddle for accurate placement of a cutting guide on a bone. Said fixtures including an attachment device for rigid connection to a second bone, attached to a second end of said linkage when a first end of said linkage is attached to said bone, to measure the relative motion between said two separate bones.

In still a further exemplary embodiment of the present disclosure, a tool for use with an instrumented link system is provided. The tool comprising a body member having a slot in a first end; and a multi-head tool member coupled to said body member. Said multi-head tool member being received in said slot of said body member and having a first head which includes a digitizing portion and a second head which includes a paddle portion. In one example, said slot is used as a cutting guide.

Additional features and advantages of the present invention will become apparent to those skilled in the art upon consideration of the following detailed description of illustrative embodiments exemplifying the best mode of carrying out the invention as presently perceived.

BRIEF DESCRIPTION OF THE DRAWINGS

The detailed description of the drawings particularly refers to the accompanying figures in which:

FIG. 2 is a perspective view of an exemplary instrumented linkage system having a bone mount attached to a first attachment device and a second attachment device;

FIG. 3 is a perspective view of an exemplary cutting guide which may be attached to the second attachment device of the instrumented linkage system of FIG. 2;

FIG. 4 is a perspective view of an exemplary digitizing tool which may be attached to the second attachment device of the instrumented linkage system of FIG. 2;

FIG. 5 is a perspective view of an exemplary paddle tool which may be attached to the second attachment device of the instrumented linkage system of FIG. 2;

FIG. 6 is a perspective view of an exemplary bone mount which may be attached to the second attachment device of the instrumented linkage system of FIG. 2;

FIG. 17 is a perspective view of a bone mount coupled to a bone and an attachment device being coupled to the bone mount;

FIG. 17A is a top view of the bone mount of FIG. 17;

FIG. 18 is a perspective view of the attachment device of FIG. 17 coupled to bone mount of FIG. 17;

FIG. 19 is a perspective view of a retractable tool base portion;

FIG. 20 is a perspective view of the retractable tool base portion of FIG. 19 having a digitizing tool coupled thereto in a retracted position;

FIG. 21 is a perspective view of the retractable tool base portion of FIG. 19 having a digitizing tool coupled thereto in an extended position;

FIG. 22 is a perspective view of the retractable tool base portion of FIG. 19 having a paddle tool coupled thereto in a retracted position;

FIG. 23 is a perspective view of the retractable tool base portion of FIG. 19 having a paddle tool coupled thereto in an extended position;

FIG. 24 is a perspective view of a head component of a combination digitizing and paddle tool;

FIG. 25 is a perspective view of the head component of FIG. 24 being held in a base component, the combination digitizing and paddle tool being placed in a paddle configuration;

FIG. 26 is a perspective view of the head component of FIG. 24 being held in a base component, the combination digitizing and paddle tool being placed in a digitizing configuration;

FIG. 34 is a perspective view of another movable coupling;

FIG. 35 is an exploded view of the movable coupling of FIG. 34;

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION OF THE DRAWINGS

The embodiments of the invention described herein are not intended to be exhaustive or to limit the invention to the precise forms disclosed. Rather, the embodiments selected for description have been chosen to enable one skilled in the art to practice the invention.

Figure 1:
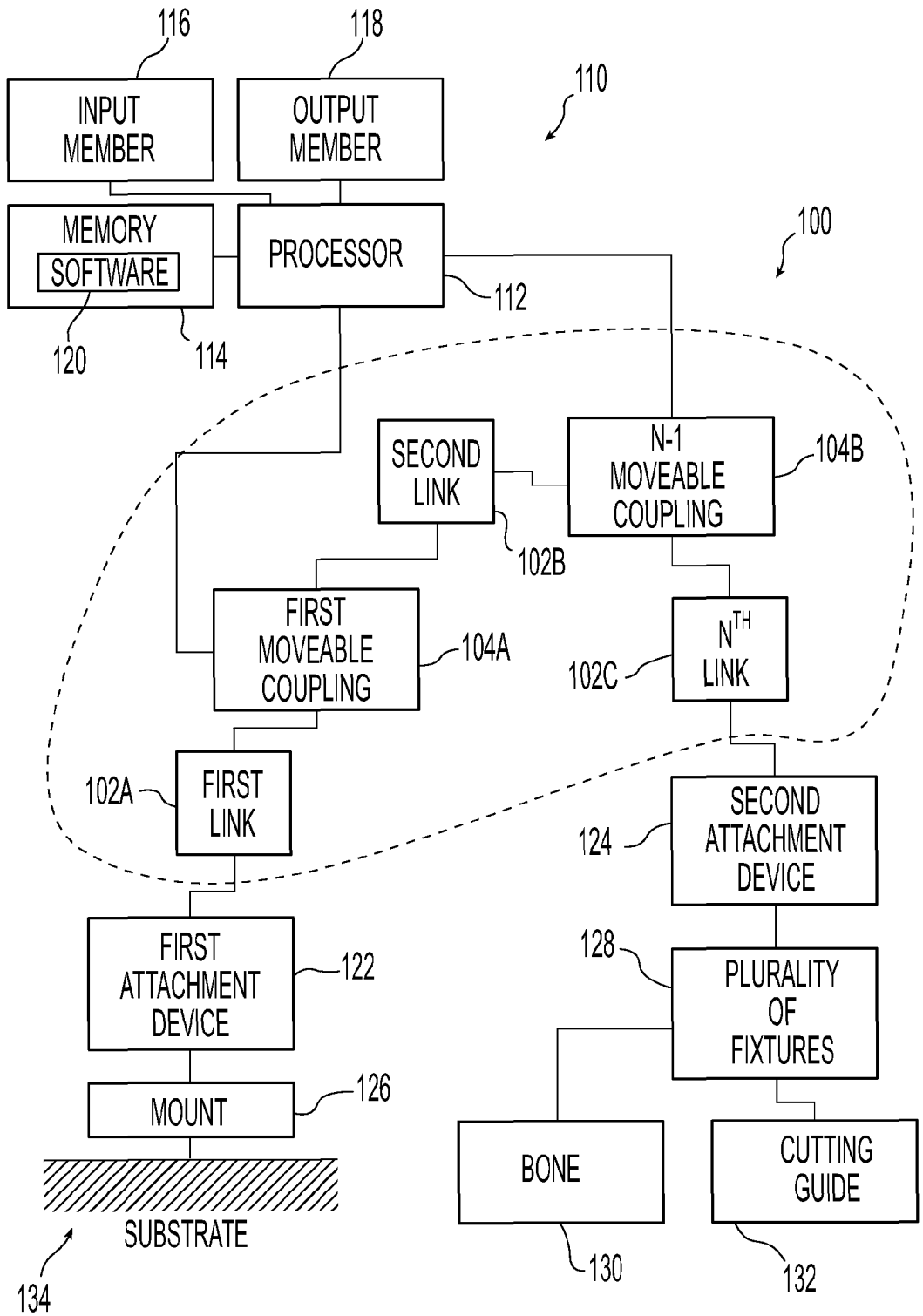
FIG. 1 is a diagrammatic representation of an instrumented linkage system, an associated controller, and associated attachment devices.

Referring to FIG. 1, an instrumented linkage 100 is shown. Instrumented linkage 100 includes a link system having a plurality of links 102 (links 102A-C shown) and a plurality of moveable couplings 104 (couplings 104A and 104B shown). Each moveable coupling 104 connects two adjacent links 102 together and provides relative movement therebetween. Exemplary moveable couplings 104 include linearly moveable couplings and rotatably moveable couplings. Each of plurality of moveable couplings 104 are operatively coupled to a processing system 110.

In one embodiment, instrumented linkage system 100 is a passive system in that none of the moveable couplings 104 are powered to cause a rotation of one of links 102 to move relative to another of links 102.

Processing system 110 includes a processor 112, a memory 114 accessible by processor 112, at least one input member 116 operatively coupled to processor 112, and at least one output member 118 operatively coupled to processor 112.

Processing system 110, in one embodiment, is wired to each of moveable couplings 104, and receives an indication of the relative rotation of each encoder in the coupling 104. Processing system 110, in one embodiment, is in wireless communication with each of movable couplings 104, and receives an indication of the relative rotation of each encoder of the coupling 104. In one embodiment, processing system 110 is provided proximate to instrumented linkage 100, such as a surgical room with the instrumented linkage 100. In one embodiment, processing system 110 is remote from instrumented linkage 100 and is in communication with instrumented linkage 100 through a network, such as a wireless network or a wired network.

In one embodiment, memory 114 is located proximate to processor 112. In one embodiment, memory 114 is accessible over network by processor 112. Exemplary at least one input member 116 include a mouse, a keyboard, a foot actuated input pedal, a touch screen, and other suitable input members. Exemplary at least one output member 118 include a display, a printer, a speaker, and other suitable output members. In one embodiment, output member 118 is a display positioned towards the second end (proximate second attachment device 124) of instrumented linkage 100. In one embodiment, output member 118 uses both light emitting diodes and a liquid crystal display screen to provide visual indications to the surgeon. In one embodiment, output member 118 is a display positioned remote from second end 182 of instrumented linkage 100. As explained herein output member 118 provides indicia of the location of a second end of instrumented linkage 100.

Each of each of link 102A and link 102B is coupled to a respective attachment device 122 and 124. Attachment devices 122 and 124 may be coupled to a plurality of accessories. Exemplary accessories include a mount 126 and any of a plurality of fixtures 128. Exemplary mounts include bone mounts and patient support mounts, such as table mounts. Exemplary fixtures include digitizing pointers, paddle tools, and other suitable fixtures. Fixtures 128 may interact with a bone 130 or a cutting guide 132. Mount 126 may interact with a substrate 134. Exemplary substrate 134 include bone, a table rail, a table top, and other suitable substrates.

An exemplary processing system 110 is a general purpose computer. Processor 112 executes software 120 which, in one embodiment, performs the methods discussed herein. In one embodiment, processor 112 by executing software 120 is configured to prompt a user of instrumented linkage 100 to couple a digitizing fixture to attachment device 124 and to locate a plurality of landmark points. Exemplary landmark points for a femur include center of distal femur, points on patella groove, distal most points on lateral and medial condyles, posterior most points on lateral and medial condyles, extreme points on lateral and medial condyles. Exemplary landmark points for a tibia include lateral and medial malleoli, lateral border of patella tendon, center of attachment of anterior cruciate ligament, center of attachment of posterior cruciate ligament, lowest point on lateral plateau, lowest point on medial plateau, extreme points on lateral and medial plateaus.

By knowing the relative lengths of each plurality of links 102 and the indications from each of plurality of moveable couplings 104, processor 112 may determine the location of an end of instrumented linkage 100. The user may provide an indication with input member 116 that the digitizing fixture is contacting a given landmark point. By knowing the relative positions of memory 114 (such as angular positions for rotary encoders) for a plurality of landmark points, software 120 is able to determine the locations of other anatomical structures including points, planes, and axes, and to determine the location of a first end of instrumented linkage 100 which is fixed to substrate 134. Once the location of the first end of instrumented linkage 100 is known, then software 120 is able to determine if the second end of instrumented linkage 100 is located in the correct location and/or orientation. For example, the second end of instrumented linkage 100 may be attached to a paddle fixture and is being used to place a cutting guide. Software 120 may in this instance have determined a target location and/or orientation for the cutting guide based on the location of the landmark points and may now provide feedback to the operator whether the second end of instrumented linkage 100 is at a location and/or orientation which corresponds to the cutting guide being at its target location and/or orientation. Further, if the second end of instrumented linkage 100 is at a location and/or orientation other than at its target location and/or orientation, software 120 may provide an indication with output member 118 of the misalignment.

Exhibit A of U.S. Provisional Application Ser. No. 60/897,809, the disclosure of which is expressly incorporated by reference herein, includes a general description of a study associated with an instrumented linkage system of the present disclosure. The study suggests the application of the instrumented linkage systems of the present disclosure to aid in a total knee replacement application.

Referring to FIG. 2, an exemplary instrumented linkage system 150 is shown. Exemplary instrumented linkage system 150 includes a first link 152 moveably coupled to a second link 154 through a first rotary coupling 166, a third link 156 moveably coupled to second link 154 through a second rotary coupling 168, a fourth link 158 moveably coupled to third link 156 through a third rotary coupling 170, a fifth link 160 moveably coupled to fourth link 158 through a fourth rotary coupling 172, a sixth link 162 moveably coupled to fifth link 160 through a fifth rotary coupling 174, a seventh link 164 moveably coupled to sixth link 162 through a sixth rotary coupling 176. Exemplary instrumented linkage system 150 includes six degrees of freedom. In one embodiment, exemplary instrumented linkage system 150 may include more or less degrees of freedom. A first end 178 of exemplary instrumented linkage system 150 includes an attachment device 180 at the end of first link 152. A second end 182 of exemplary instrumented linkage system 150 includes an attachment device 184 at the end of seventh link 164.

Attachment device 180 and attachment device 184 are bosses which having a recess (see FIG. 19 for recess 213 in attachment boss 184) for receiving a shaft of an accessory. As shown in FIG. 2, a bone mount 188 is shown having a shaft 190 received by a recess of attachment device 180 (same as recess 213 in attachment device 184 in FIG. 19). Attachment device 180 and attachment device 184 each include an aperture 192 and 194, respectively, which receives a fastener (not shown) to couple the shaft of the accessory to the respective attachment device. An exemplary fastener would be a set screw. Referring to FIG. 6, bone mount 188 includes an aperture 191 in shaft 190 for receiving the fastener.

By knowing the relative angular positions of moveable couplings 166, 168, 170, 172, 174, and 176 and the lengths of links 152, 154, 156, 158, 160, 162, and 164 (including the lengths of the accessories attached to links 152 and 164), processing system 110 is able to determine the location of one of the endpoint of one of link 152 and seventh link 164 as well as its orientation. Therefore, by knowing the location of bone mount 188 affixed to a bone, processing system 110 may determine the location and orientation of seventh link 164 which may be supporting an accessory (and hence the location and orientation of the accessory).

Referring to FIG. 3, an exemplary cutting guide 196 is shown. Cutting guide 196 includes a shaft 198 which may be coupled to attachment device 184. Cutting guide 196 may be used to guide a cut for a surgical operation, such as a cut in total knee replacement. Additional details regarding exemplary cutting guide 196 are provided with reference to FIGS. 27-29.

Referring to FIG. 4, a tool base 200 is shown having a digitizing tool 201 coupled thereto. Tool base 200 includes a shaft 202 which may be coupled to attachment device 184. Digitizing tool 201 may be used to locate landmark points on one or more portions of an anatomy of a patient.

In one embodiment, processing system 110 prompts the user for a desired landmark point, the user touches the landmark point with a tip of digitizing tool 201, and the user provides an input to processing system 110 with input member 116 to indicate that the tip of digitizing tool 201 is at the landmark point. Processing system 110 then notes the positions of each of the moveable couplings of instrumented linkage system 150 as corresponding to the requested landmark point. Based on knowing the positions of each of the moveable couplings of instrumented linkage system 150 for a plurality of landmark points, processing system 110 may infer the location of bone mount 188 and also infer the position of paddle tool 204 or other tools attached to the end of instrumented linkage system 150.

Referring to FIG. 19, tool base 200 is shown spaced apart from attachment device 184. Attachment device 184 includes a recess 213 which receives shaft 202. In one embodiment, tool base 200 is coupled to attachment device 184 with a fastener which is threaded into aperture 194 of attachment device 184 and engages with recess 203 in shaft 202. Other suitable methods of fastening shaft 202 to attachment device 184 may be used. For example, shaft 202 and recess 213 of attachment device 184 are each threaded and shaft 202 is threaded into recess 213. Other suitable, fastening methods include quick connect fasteners and other suitable fasteners.

Referring to FIGS. 20 and 21, digitizing tool 201 is shown coupled to tool base 200. Digitizing tool 201 is received in a channel 214 provided in tool base 200. Digitizing tool 201 is shown in a retracted position in FIG. 20 and in an extended position in FIG. 21. In the retracted position, digitizing tool 201 may be used to digitize points in the knee joint. In the extended position, digitizing tool 201 may be used to digitize the ankle region and to determine the center of the femoral head.

In one embodiment, digitizing tool 201 is coupled to tool base 200 through a fastener which is threaded into aperture 216 in tool base 200 and which engages digitizing tool 201. In the retracted position, digitizing tool 201 is abutted against an end wall 218 of channel 214 and the fastener engages the cylindrical wall of digitizing tool 201. In the extended position a recess 220 of digitizing tool 201 is aligned with aperture 216 and the fastener is advanced into recess 220. In one embodiment, digitizing tool 201 may have a plurality of recesses 220 to correspond to a plurality of extended positions and/or the retracted position. In one embodiment, the user must inform processing system 110 whether digitizing tool 201 is in the extended position or the retracted position. In one embodiment, processing system 110 instructs the operator to place digitizing tool 201 in one of the extended position and the retracted position.

Referring to FIG. 5, a paddle tool 204 is shown. Paddle tool 204 includes a shaft 206 which may be coupled to tool base 200 for attachment to attachment device 184. Paddle tool 204 may be used to locate exemplary cutting guide 196 relative to one or more portions of an anatomy of a patient and/or to check the accuracy of one or more cuts performed on one or more portions of an anatomy of a patient.

Referring to FIGS. 22 and 23, paddle tool 204 is shown coupled to tool base 200. Paddle tool 204 is received in channel 214 provided in tool base 200. Paddle tool 204 is shown in a retracted position in FIG. 22 and in an extended position in FIG. 23. In the retracted position, paddle tool 204 may be used for docking in a slot of a cutting guide to determine the accuracy of the placement of the cutting guide. In the extended position, paddle tool 204 may be used to measure a flatness of a cut surface.

In one embodiment, paddle tool 204 is coupled to tool base 200 through a fastener which is threaded into aperture 216 in tool base 200 and which engages paddle tool 204. In the retracted position, paddle tool 204 is abutted against an end wall 218 of channel 214 and the fastener engages the cylindrical wall of paddle tool 204. In the extended position a recess 222 of paddle tool 204 is aligned with aperture 216 and the fastener is advanced into recess 222. In one embodiment, paddle tool 204 may have a plurality of recesses 220 to correspond to a plurality of extended positions and/or the retracted position. In one embodiment, the user must inform processing system 110 whether paddle tool 204 is in the extended position or the retracted position. In one embodiment, processing system 110 instructs the operator to place paddle tool 204 in one of the extended position and the retracted position.

Referring to FIGS. 24-26, a combination tool 400 is shown. Combination tool 400 includes a body 402 which, in one embodiment, may be coupled to instrumented linkage 100. Body 402 includes a slot 404. Slot 404 receives a two headed tool member 406 which includes a base portion 408, a digitizing portion 410, and a paddle portion 412. In one embodiment, two headed tool member 406 is coupled to body 402 by a pin which is received in aperture 414 of two headed tool member 406 and an aperture 416 of body 402. Combination tool 400 is a paddle tool when two headed tool member 406 is rotated relative to body 402 such that paddle portion 412 extends outward from body 402, as illustrated in FIG. 25. Combination tool 400 is a digitizing tool when two headed tool member 406 is rotated relative to body 402 such that digitizing portion 410 extends outward from body 402, as illustrated in FIG. 26. In one embodiment, two headed tool member 406 may be removed from body 402 and slot 404 used as a drill guide.

Figure 7:
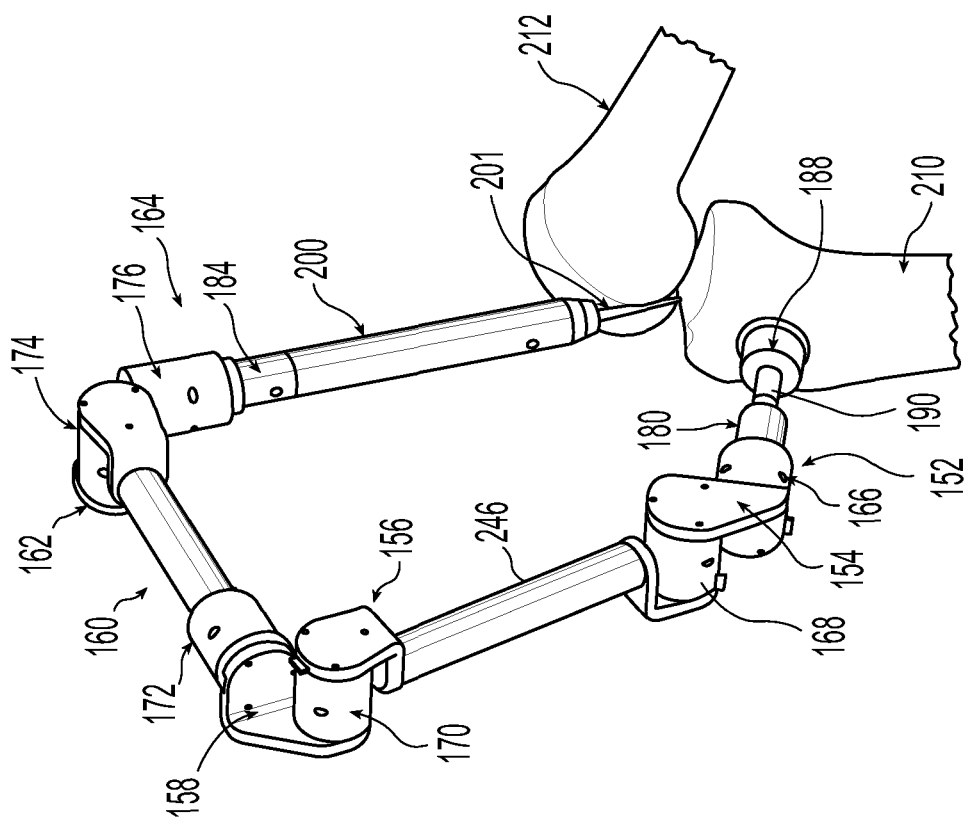
FIG. 7 is a perspective view of the instrumented linkage system of FIG. 2 coupled to a tibia bone and having the digitizing tool of FIG. 4 attached to a second end of the instrumented linkage system.
Figure 8:
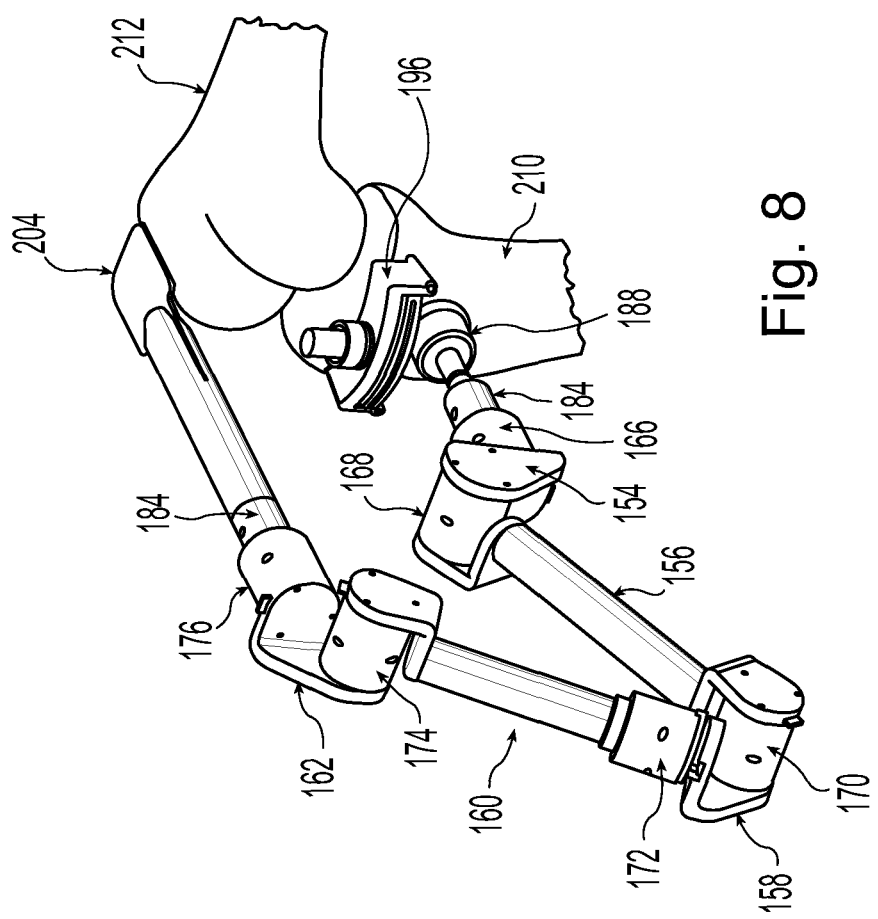
FIG. 8 is a perspective view of the instrumented linkage system of FIG. 2 coupled to a tibia bone and having the paddle tool of FIG. 5 attached to a second end of the instrumented linkage system and the cutting guide of FIG. 3 coupled to the tibia bone.

Referring to FIG. 7, instrumented linkage 100 is shown with a digitizing tool 201 attached to attachment device 184. Digitizing tool 201 may be used to digitize a plurality of landmark points on a bone, such as tibia bone 210 and femur bone 212 illustrated in FIG. 7. Further, instrumented linkage 100 is shown attached to tibia bone 210 through bone mount 188. Referring to FIG. 8, instrumented linkage 100 is shown with paddle tool 204 attached to attachment device 184. Paddle tool 204 may be used to make fine adjustments to the placement of exemplary cutting guide 196 on tibia bone 210.

Each of moveable couplings 166, 168, 170, 172, 174, and 176 is a rotatable coupling which permits the relative rotation of one link relative to an adjacent link. The structure and operation of moveable couplings 166, 168, 170, 172, 174, and 176 are discussed in more detail in connection with FIGS. 12-16.

Figure 9:
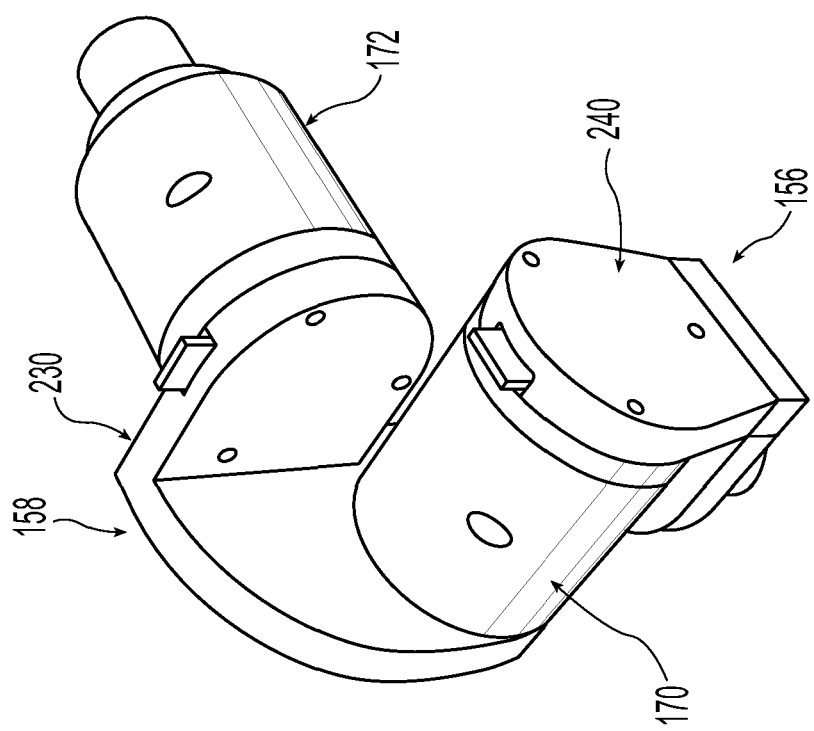
FIG. 9 is a perspective view of a pair of moveable couplings and a pair of links of the instrumented linkage system of FIG. 2.
Figure 10:
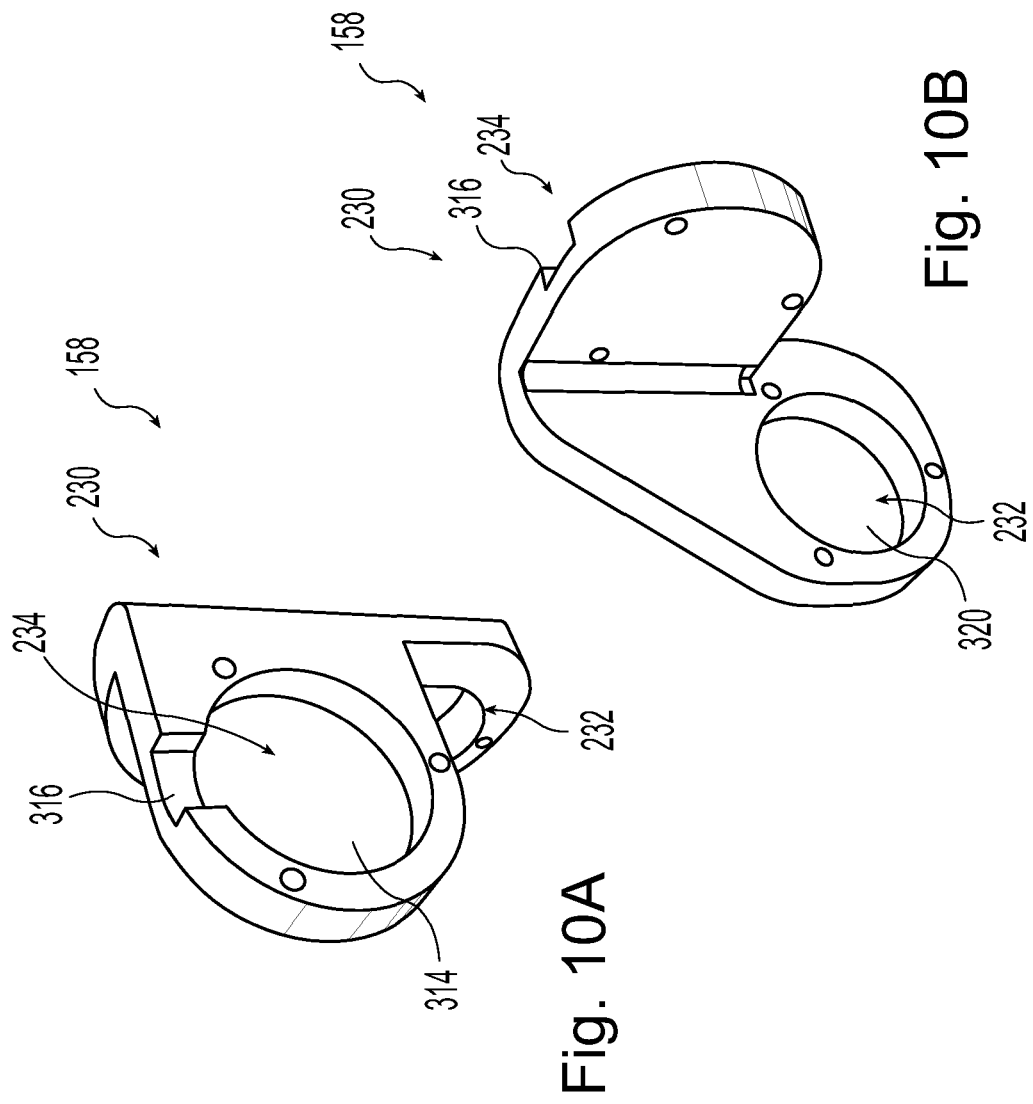
FIG. 10A is a first perspective view of a first link of FIG. 9 of the instrumented linkage system of FIG. 2.
FIG. 10B is a second perspective view of the first link of FIG. 10A.

Referring to FIG. 9, third rotary coupling 170 and fourth rotary coupling 172 are shown along with third link 156 and fourth link 158. Fourth link 158 is an angle bracket 230. Referring to FIGS. 10A and 10B, angle bracket 230 includes a first attachment portion 232 for attaching third rotary coupling 170 and a second attachment portion 234 for attaching fourth rotary coupling 172. Each of third rotary coupling 170 and fourth rotary coupling 172 may be attached with fasteners which are threaded into apertures in the respective first attachment portion 232 and 234, and then into the housing of the respective third rotary coupling 170 and fourth rotary coupling 172.

Figure 11:
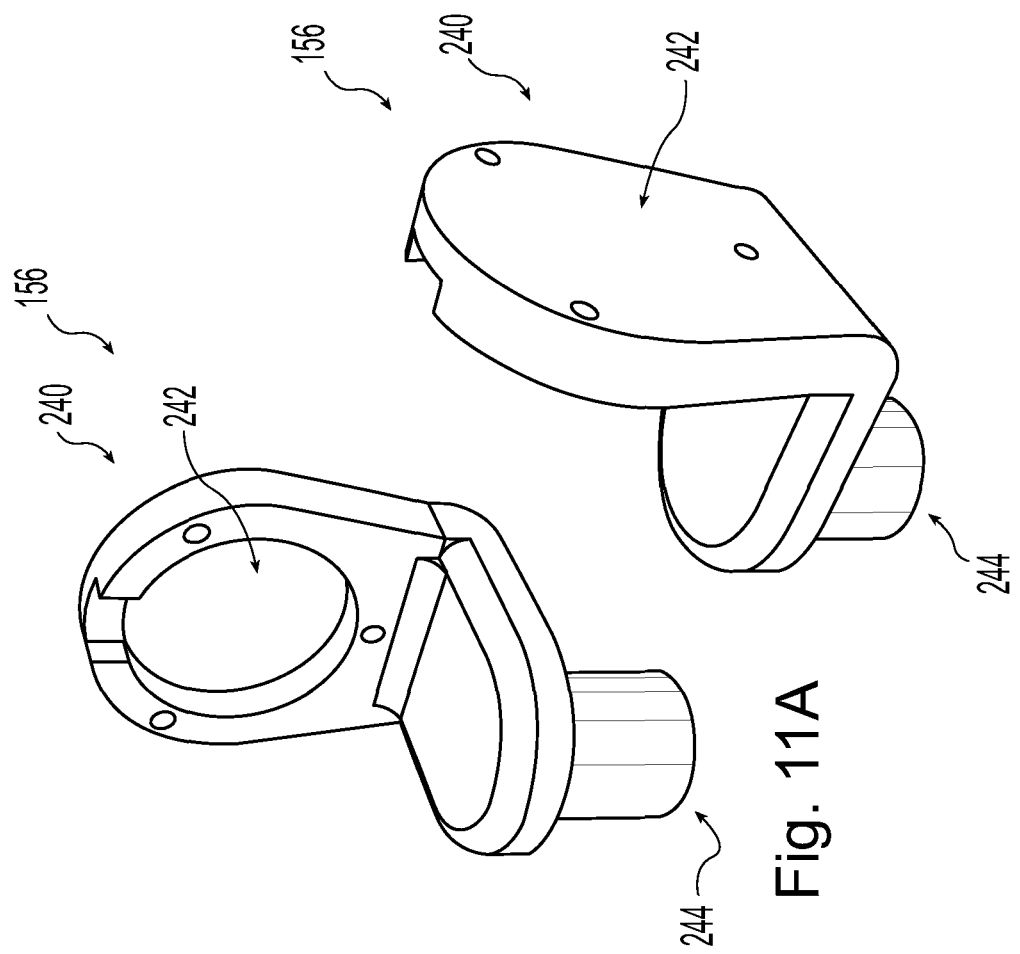
FIG. 11A is a first perspective view of a second link of FIG. 9 of the instrumented linkage system of FIG. 2.
FIG. 11B is a second perspective view of the second link of FIG. 11A.

Third link 156 includes an angle bracket 240 and an elongated portion 246. Referring to FIGS. 11A and 11B, angle bracket 240 includes a first attachment portion 242 for attaching third rotary coupling 170 and a second attachment portion 244 for attaching elongated portion 246. Each of third rotary coupling 170 and elongated portion 246 may be attached with fasteners which are threaded into apertures in the respective first attachment portion 242 and 244, and then into the housing of third rotary coupling 170 and into elongated portion 246, respectively. Elongated portion 246 is further coupled to second rotary coupling 168 through a second angle bracket 240 of third link 156 as shown in FIG. 2.

Referring to FIGS. 12-16, the structure and operation of moveable couplings 166, 168, 170, 172, 174, and 176 are discussed in more detail. Each of moveable couplings 166, 168, 170, 172, 174, and 176 operate in the same manner. The structure and operation of fourth rotary coupling 172 is explained in FIGS. 12-16.

Figure 12:
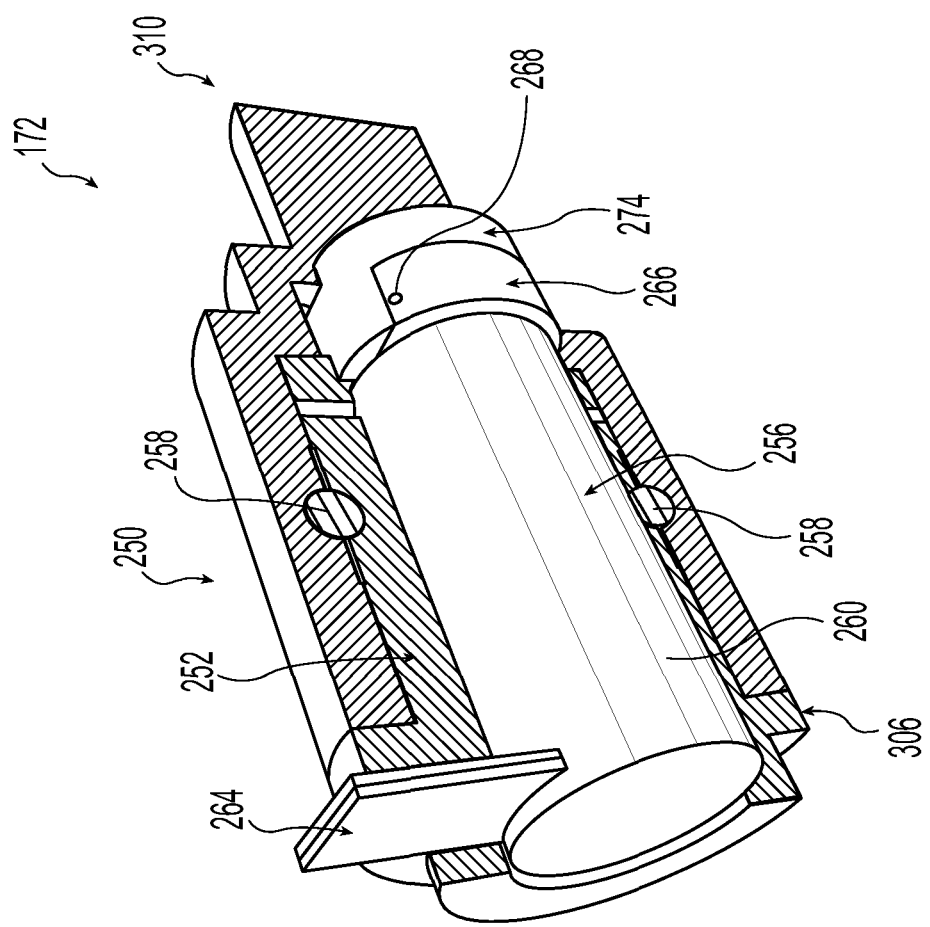
FIG. 12 is a perspective view of a moving coupling of the instrumented linkage system of FIG. 2.
Figure 13:
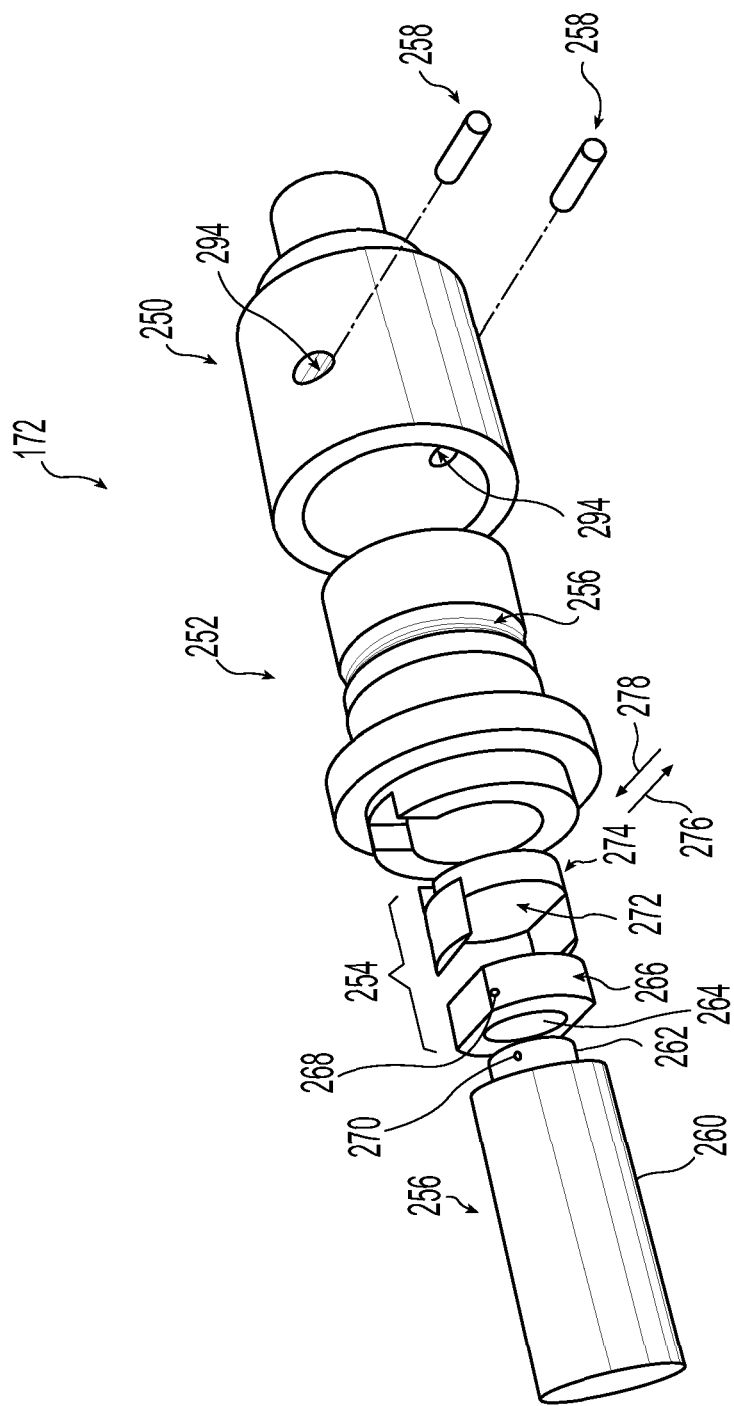
FIG. 13 is an exploded view of a moving coupling of the instrumented linkage system of FIG. 2.
Figure 14:
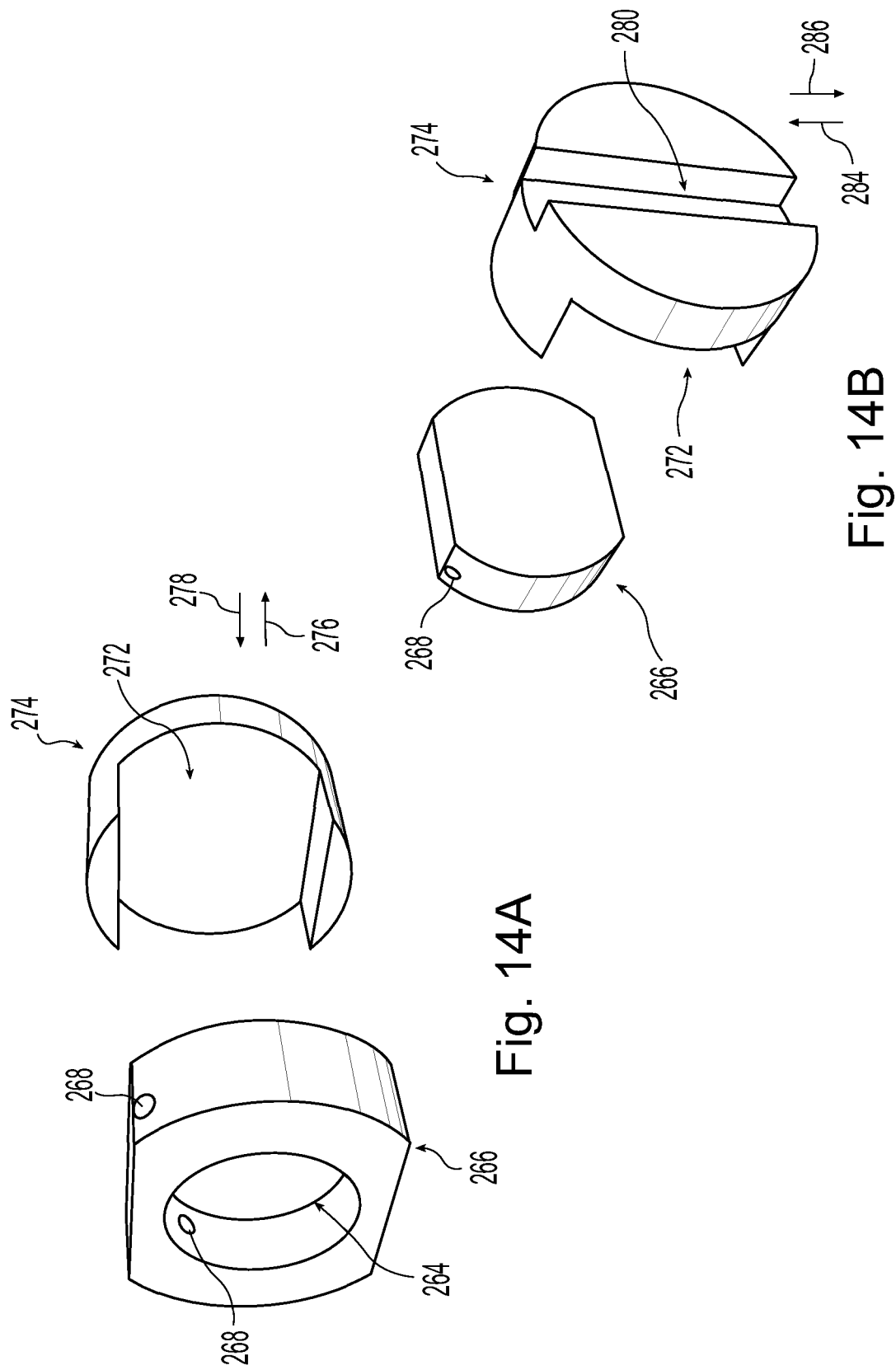
FIG. 14A is a first exploded view of a freedom coupling of the moving coupling of FIG. 12.
FIG. 14B is a second exploded view of a freedom coupling of the moving coupling of FIG. 12.

Referring to FIG. 13, fourth rotary coupling 172 is shown. Fourth rotary coupling 172 includes a first housing 250, a second housing 252, a coupling 254, a rotary encoder 256, and a pair of retainers 258. Rotary encoder 256 includes a body 260 and a rotatable boss 262. Rotary encoder 256 is able to measure the relative rotation of rotatable boss 262 relative to body 260 and to provide an indication of that rotation to processing system 110 through a connection. In one embodiment, the connection is a wired connection 264, such as a ribbon cable, whose location is indicated in FIG. 12. In one embodiment, the connection is a wireless connection. In order for fourth rotary coupling 172 to measure the relative rotation between fourth link 158 and fifth link 160, one of body 260 and rotatable boss 262 needs to be responsive to the position of fourth link 158 and the other of body 260 and rotatable boss 262 needs to be responsive to the position of fifth link 160.

Rotatable boss 262 is received in a recess 264 of a first coupling member 266 of coupling 254. Rotatable boss 262 is secured to first coupling member 266 with a pair of screws which are threaded into openings 268 in first coupling member 266 and openings 270 in rotatable boss 262. First coupling member 266 is received in a channel 272 of a second coupling member 274. First coupling member 266 is moveable relative to second coupling member 274, but is constrained to move only in direction 276 and direction 278.

Figure 16:
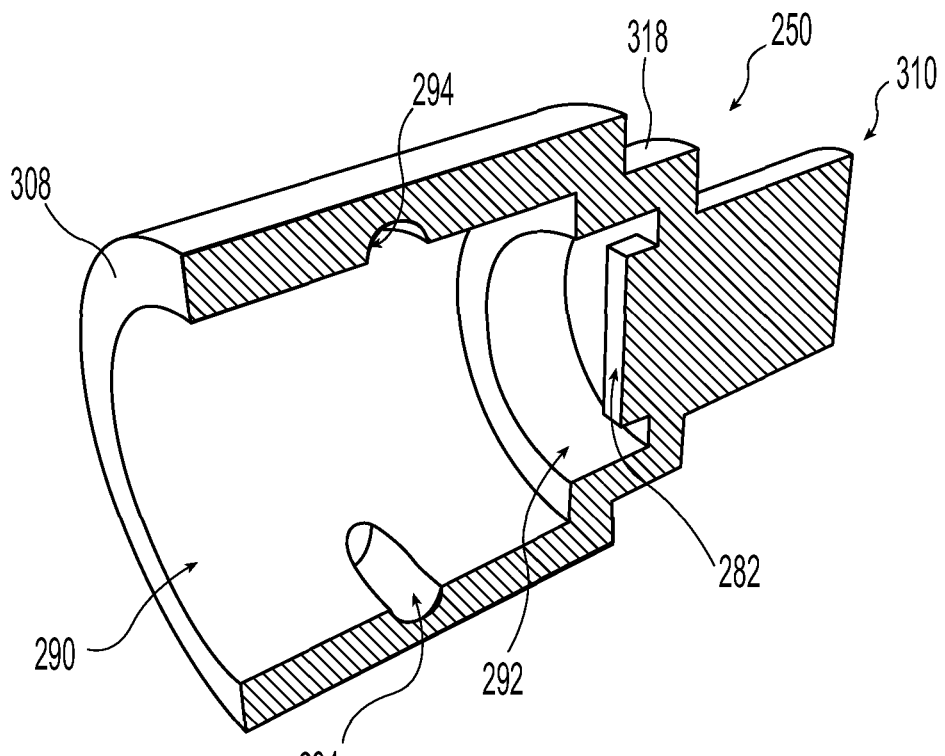
FIG. 16 is a partial view of a rotating housing of the moving coupling of FIG. 12.

Second coupling member 274 further includes a channel 280 which interacts with a protrusion 282 on first housing 250 (see FIG. 16). The interaction between channel 280 and protrusion 282 constrains the movement of second coupling member 274 relative to first housing 250 in direction 284 and direction 286.

Referring to FIG. 16, first housing 250 includes a cavity 290 which includes a pocket 292 into which protrusion 282 extends. Pocket 292 receives second coupling member 274 such that channel 280 engages protrusion 282. In one embodiment, a small clearance is provided between channel 280 and protrusion 282 to minimize any axial force on rotary encoder 256. In one example, the clearance is about 0.25 mm.

Cavity 290 also receives second housing 252. A pair of retainers 258 are placed through openings 294 in first housing 250 and are received partially in a circumferential groove 296 in second housing 252 to retain second housing 252 relative to first housing 250. Second housing 252 is free to rotate relative to first housing 250, but is not translatable relative to first housing 250.

Figure 15:
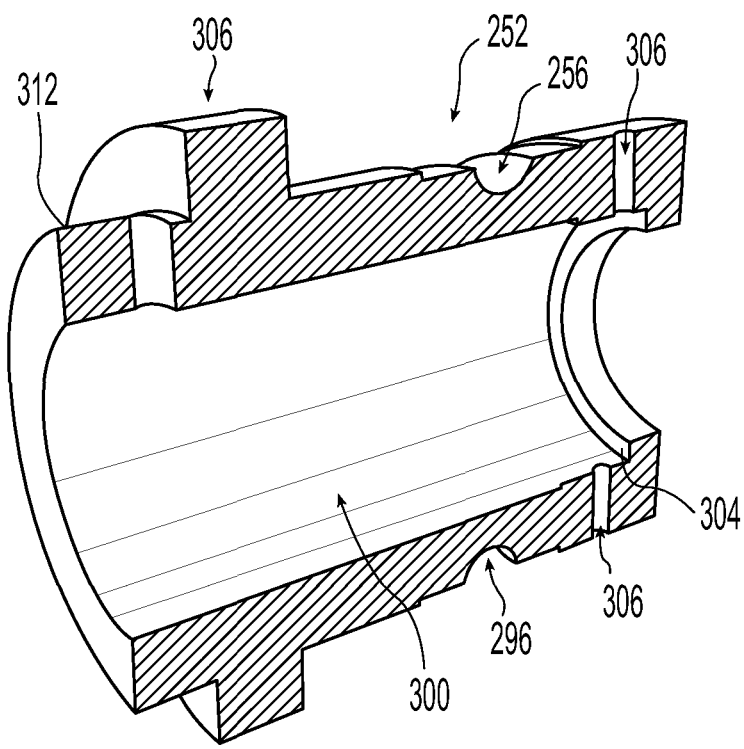
FIG. 15 is a partial view of an encoder housing of the moving coupling of FIG. 12.

Referring to FIG. 15, second housing 252 includes a cavity 300 which receives rotary encoder 256. A reduced diameter portion 302 of cavity 300 supports first coupling member 266. An end of body 260 abuts against an end surface 304 of cavity 300. Fasteners, such as screws, are presented in openings 304 in second housing 252 and tighten against body 260 to retain rotary encoder 256 relative to second housing 252. A flange 306 of second housing 252 abuts against an end surface 308 of first housing 250 when assembled.

In one embodiment, fourth rotary coupling 172 is assembled in the following manner. First coupling member 266 of coupling 254 is attached to rotatable boss 262 and secured with a pair of screws received in apertures 268 of first coupling member 266 and openings 270 of rotatable boss 262. Rotary encoder 256 is then slid into second housing 252 and secured in place with screws threaded into flange 306. First housing 250 is slid onto second housing 252 so that channel 280 in second coupling member 274 receives protrusion 282 of first housing 250. A pair of retainers 258 are then placed in openings 294 to retain second housing 252 from moving axially relative to first housing 250.

Coupling 254 reduces the force exerted on rotatable boss 262 of rotary encoder 256. By allowing first coupling member 266 to move in direction 276 and direction 278 and second coupling member 274 to move in direction 284 and direction 286, the radial forces exerted on rotatable boss 262 due to the movement of one of rotatable boss 262 relative to body 260 is minimized. In one embodiment, first coupling member 266 is made of a plastic material and channel 272 is made of stainless steel.

Referring to FIG. 15, second housing 252 includes a flange 312 which is received in a pocket portion 314 of second attachment portion 234 of angle bracket 230. The wiring 264 from rotary encoder 256 is communicated through a recess 316 of second attachment portion 234. Referring to FIG. 16, first housing 250 includes a boss 310 which may be coupled to elongated portion 246 through a fastener. For some moveable coupling, such as third rotary coupling 170, boss 310 is removed and a flange 318 of first housing 250 is received in a pocket portion 320 of first attachment portion 232.

Referring to FIGS. 34-37, another exemplary embodiment of a moveable coupling 340 is shown. Two instances of moveable coupling 340 are shown housed in a common housing 342 which serves as an intermediate link between the two instances of moveable coupling 340. Referring to FIG. 35, moveable coupling 340 includes a rotary encoder 344, a housing pin 346, an encoder mount ring 348, a first bearing 350, spacers 352, a second bearing 354, and a housing ring 356. Moveable coupling 340 permits the movement of a second housing 358 relative to common housing 342. The other instance of moveable coupling 340 permits the movement of a third housing 360 relative to common housing 342.

Referring to FIG. 35, housing pin 346 is pressed into second housing 358 and is received in a slot 360 in rotary encoder 344. A first portion 362 of rotary encoder 344 is rotatable relative to a second portion 364 of rotary encoder 344. A mount tab 366 of second portion 364, is coupled to encoder mount ring 348. Encoder mount ring 348 is coupled to common housing 342 through a plurality of fasteners 368. First portion 362 is coupled to second housing 358 through housing pin 346.

First bearing 350 and second bearing 354 radially separate common housing 342 and second housing 358. Spacers 352 separate first bearing 350 and second bearing 354. Housing ring 356 maintains the position of first bearing 350, spacers 352, and f354 and couples second housing 358 and common housing 342 together.

As shown in FIG. 7, in one embodiment, exemplary instrumented linkage system 150 is coupled to tibia bone 210 through bone mount 188. Referring to FIGS. 17-18, the coupling of bone mount 188 to tibia bone 210 is described.

Referring to FIG. 17, bone mount 188 includes a first member 370 which is attached to tibia bone 210 and a second member 372 including shaft 190. First member 370 includes an aperture which receives a fastener 374 that couples first member 370 to tibia bone 210. In one embodiment, fastener 374 is a Cancellous screw. First member 370 also includes feet 376 which press against tibia bone 210 to prevent the rotation of first member 370 relative to tibia bone 210. First member 370 further includes threads 378 which engage mating threads on a cap 380. In one embodiment, first member 370 is about 25 mm in diameter. In one embodiment, first member 370 is about 15 mm in diameter.

First member 370 includes a locator 382 which cooperates with a locator 384 on second member 372 to prevent the rotation of second member 372 relative to first member 370. Illustratively, locator 382 and locator 384 are a pin and mating groove, respectively. Once locator 382 has been received by locator 384, cap 380 is threaded onto threads 378 to secure second member 372 to first member 370.

Figure 27:
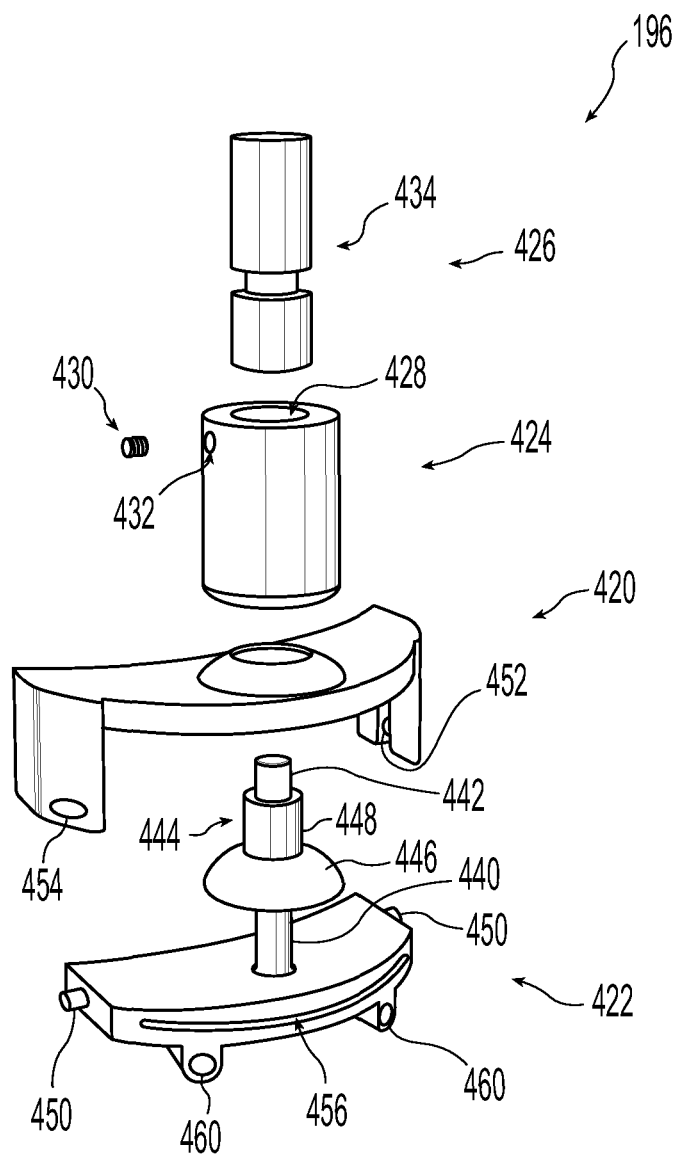
FIG. 27 is an exploded, perspective view of a first cutting guide.
Figure 28:
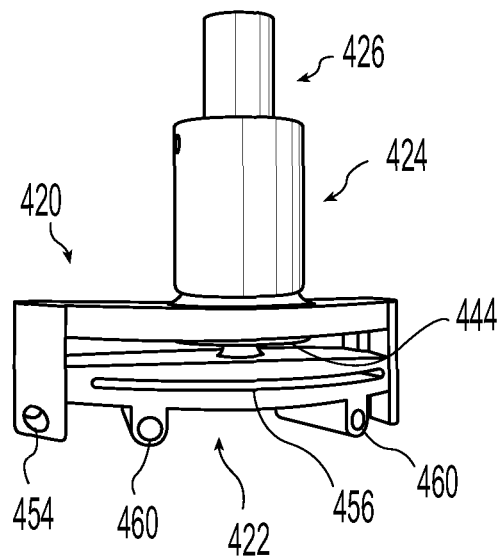
FIG. 28 is an assembled, perspective view of the first cutting guide of FIG. 27.
Figure 29:
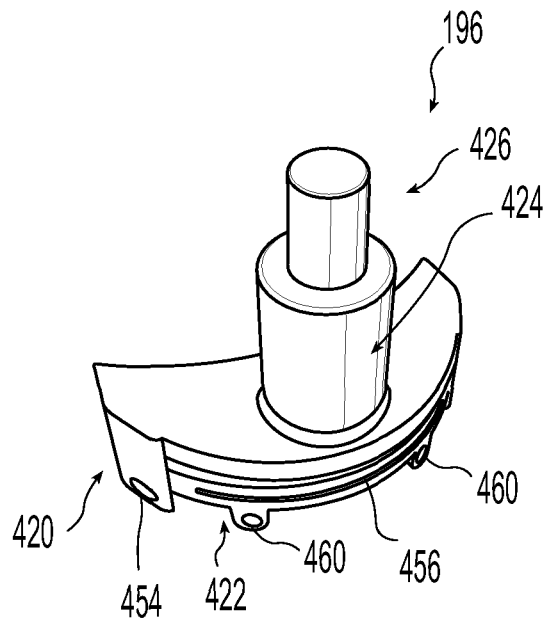
FIG. 29 is a second, perspective view of the first cutting guide of FIG. 27.
Figure 30:
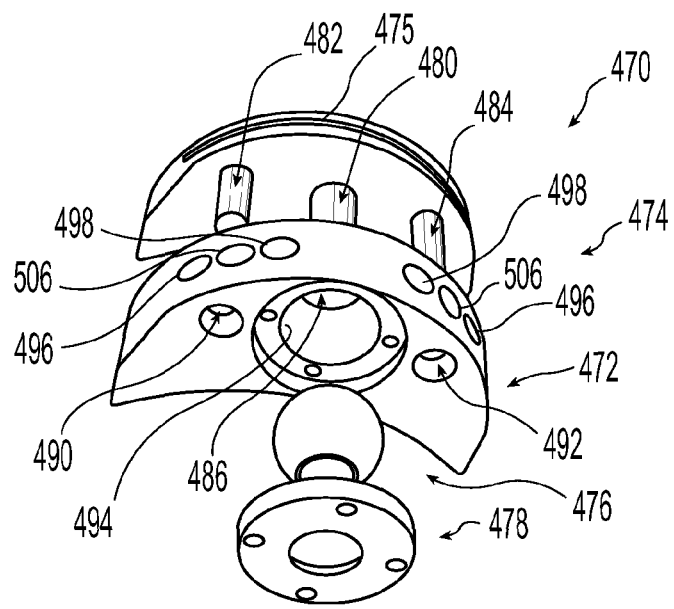
FIG. 30 is a first, exploded perspective view of a second cutting guide.
Figure 31:
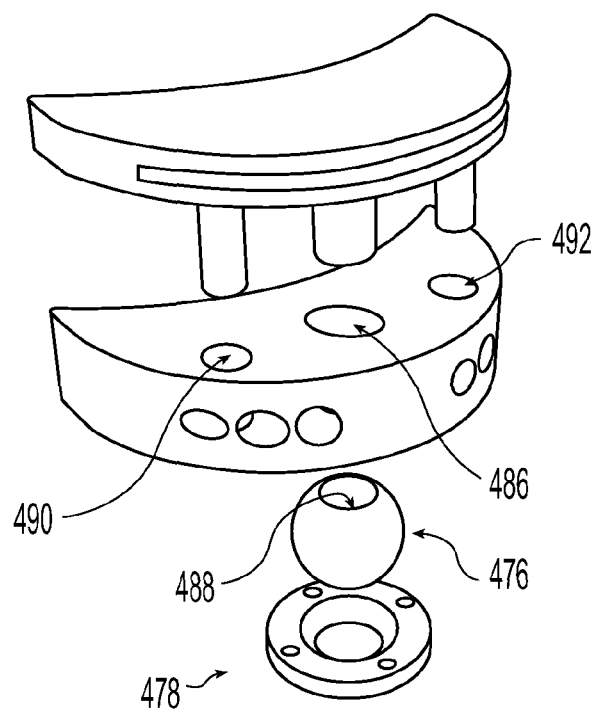
FIG. 31 is a second, exploded perspective view of the second cutting guide of FIG. 30.
Figure 32:
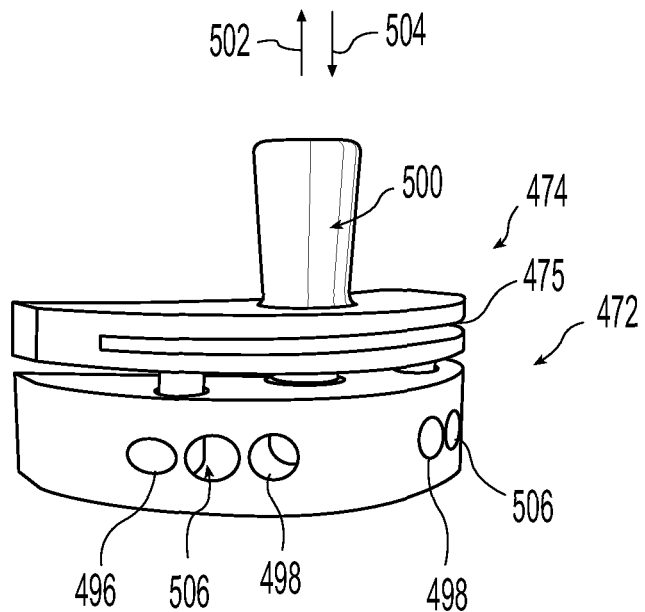
FIG. 32 is a first, assembled perspective view of the second cutting guide of FIG. 30.
Figure 33:
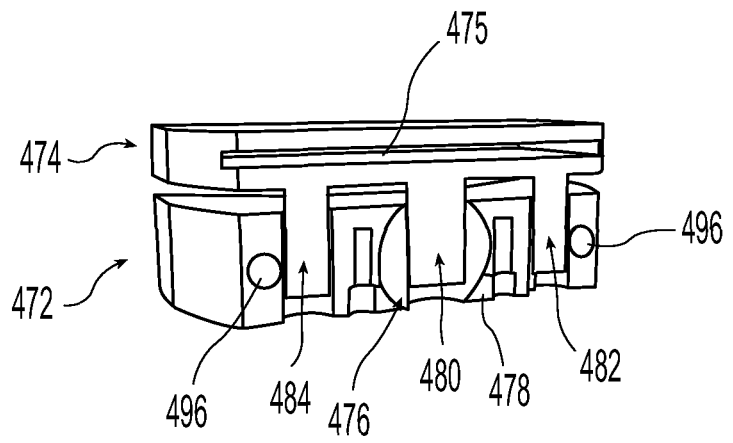
FIG. 33 is a second, assembled perspective view of the second cutting guide of FIG. 30.
Figure 37:
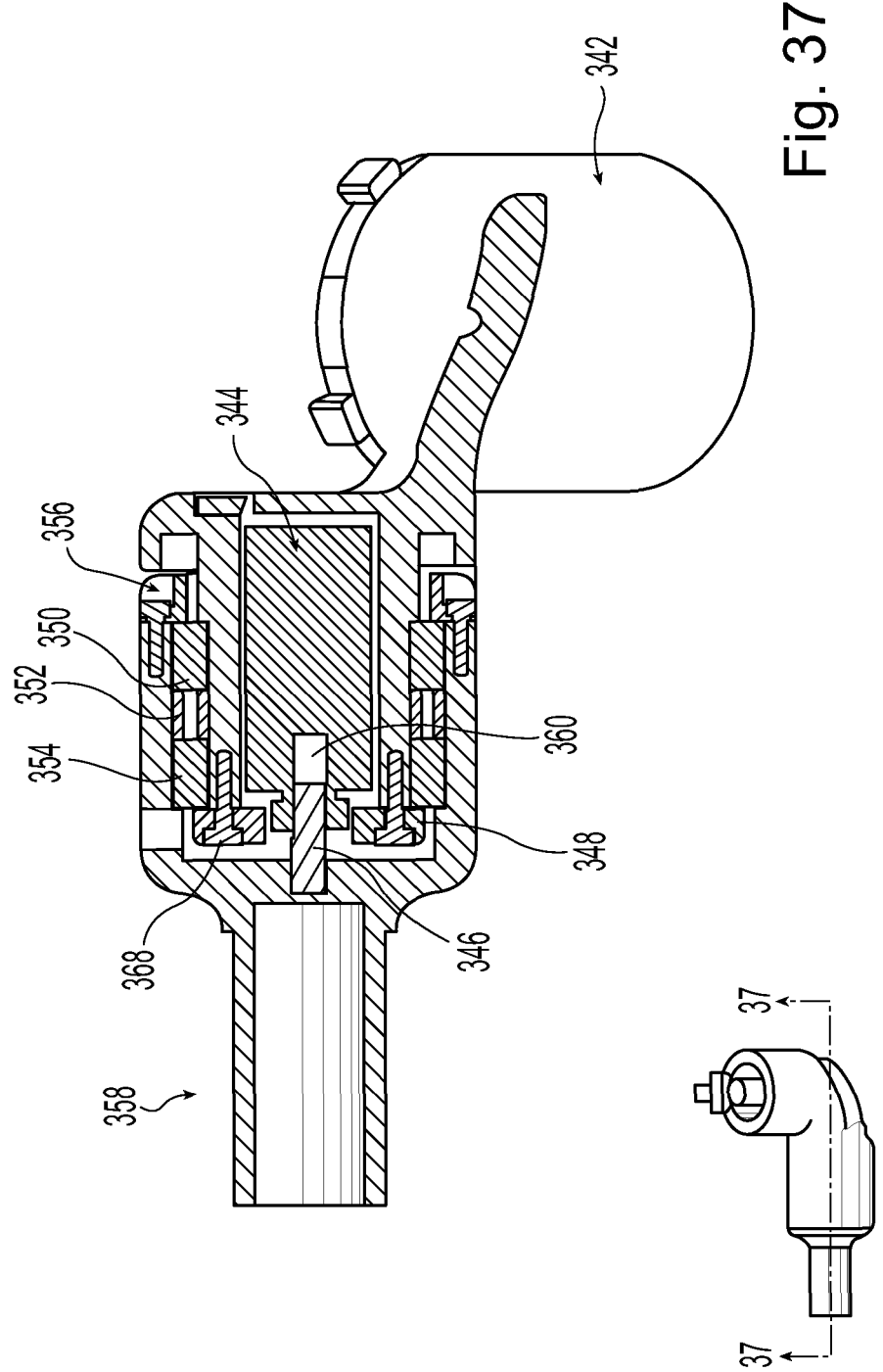
FIG. 37 is a sectional view of the movable coupling of FIG. 36 along lines 37-37 of FIG. 36.
Figure 36:
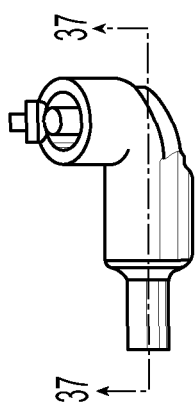
FIG. 36 is another perspective view of the movable coupling of FIG. 34.

Referring to FIGS. 27-29, cutting guide 196 is shown. Cutting guide 196 includes a frame 420, a guide member 422, an angle turret 424, and a height screw 426. Height screw 426 is received in a channel 428 of angle turret 424. A set screw 430 is threaded into an aperture 432 of angle turret 424 and is received in a groove 434 of height screw 426.

A stem 440 extends upward from guide member 422. Stem 440 includes an upper portion 442 which is threaded to mate with internal threads in groove 434. A boss 444 is placed over stem 440. Boss 444 includes a spherical surface 446 and an threaded portion 448. Spherical surface 446 mates with a corresponding spherical surface on the lower side of frame 420. Threaded portion 448 mates with internal threads in angle turret 424. Guide member 422 further includes a pair of locators 450 which are received in locators 452 of frame 420.

In operation, cutting guide 196 is coupled to the bone, such as tibia bone 210. In one embodiment, cutting guide 196 is coupled by passing screws or pins into apertures 454 of frame 420. The initial placement of cutting guide 196 may be a rough approximation of the final placement of a cutting guide slot 456 in guide member 422. In one embodiment, cutting guide 196 is roughly placed by coupling top portion 198 of cutting guide 196 to instrumented linkage 100 and locating cutting guide 196 in the approximate final location. In one embodiment, cutting guide 196 is roughly placed by coupling paddle tool 204 to instrumented linkage 100, placing paddle tool 204 in cutting guide slot 456, and locating cutting guide 196 in the approximate final location. In one embodiment, cutting guide 196 is roughly placed through operator judgment.

Once frame 420 is coupled to tibia bone 210, paddle tool 204 is coupled to instrumented linkage 100 and inserted into cutting guide slot 456. Angle turret 424 is rotated to permit the movement of boss 444 relative to frame 420. Once cutting guide slot 456 is in the correct angular orientation, instrumented linkage 100 will provide an indication to the operator. The operator will then rotate angle turret 424 to tighten boss 444 against frame 420 and lock in the angles. In the case of tibia bone 210, the angles would be the varus/valgus deviations and the flex extension angle.

Figure 44:
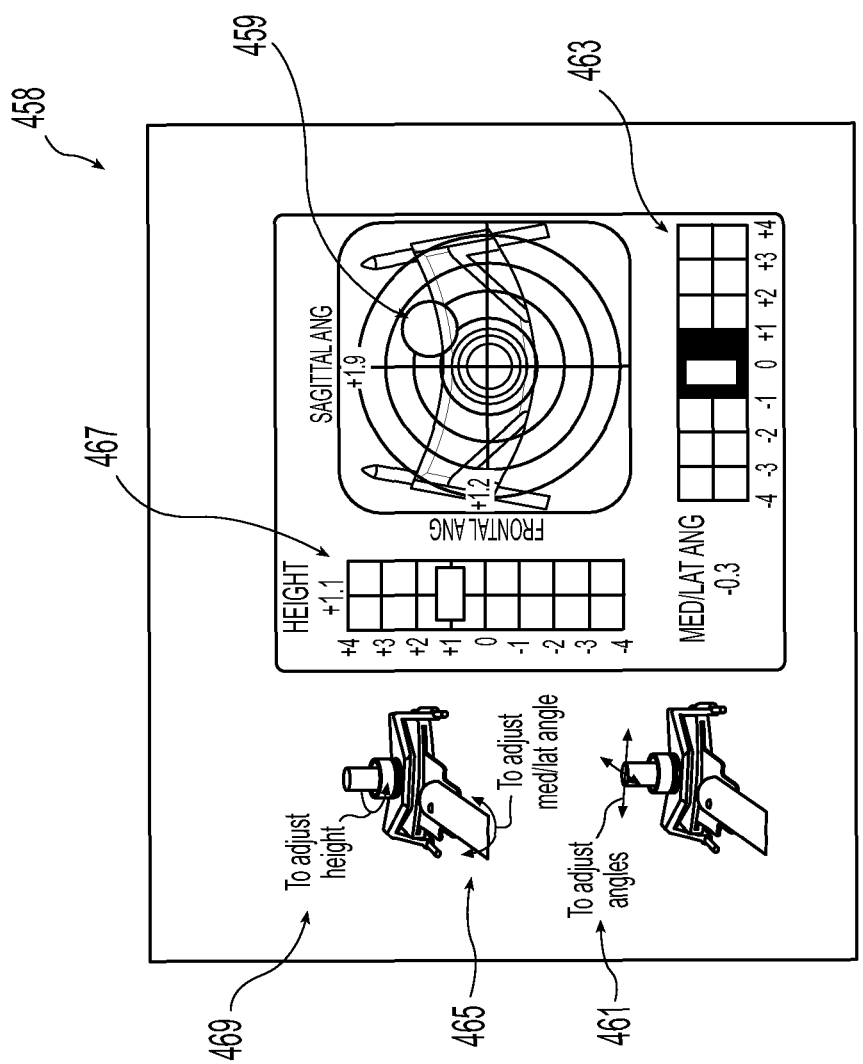
FIG. 44 is a screen display illustrating the placement of the cutting guide of FIG. 27.

The operator will then turn height screw 426 to adjust the height of cutting guide slot 456. In one embodiment, the angular and height alignment of cutting guide slot 456 relative to tibia bone 210 is achieved with an alignment guide 458 presented by processing system 110 and illustrated in FIG. 44. This alignment guide 458 is discussed herein. Once properly positioned, screws or pins are placed in apertures 460 of guide member 422 and screwed into tibia bone 210 to lock the placement of cutting guide slot 456 relative to tibia bone 210. At this point, all portions of exemplary cutting guide 196 may be removed except for guide member 422.

Figure 43:
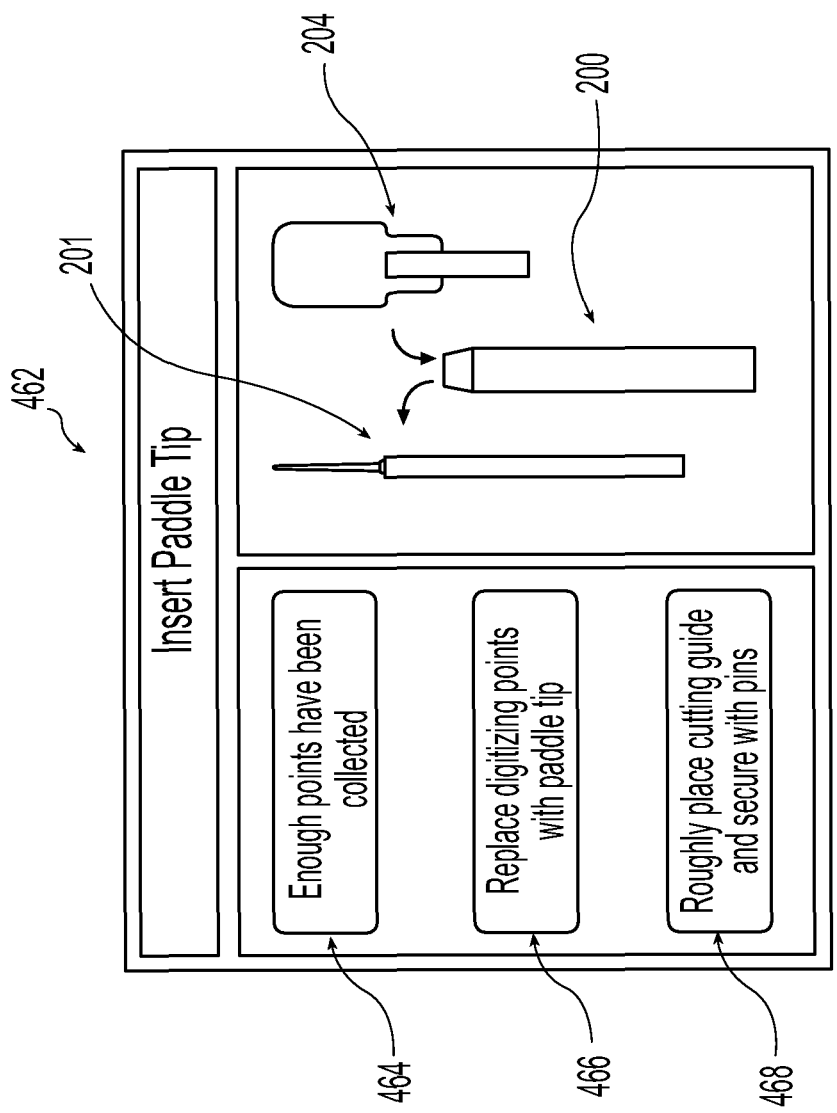
FIG. 43 is a screen display providing instructions for tool changes.

Exemplary instrumented linkage system 150 may be used in computer aided surgery applications. Processing system 110 may provide the surgeon with various screen displays on a display version of output member 118 during the computer aided surgery. Referring to FIG. 43, an exemplary screen display 462 is shown. During computer aided surgery, instrumented linkage system 150 is coupled to a substrate 134, such as a bone 130. The instrumented linkage system 150 is then used with digitizing tool 201 to digitize points on bone 130 or an adjacent bone to determine the anatomical structure of bone 130 or the adjacent bone. Screen 462 includes a first indicia 464 to indicate to the surgeon when enough points have been collected. At this point, indicia 464 is displayed or otherwise highlighted. The surgeon is then presented with an indicia 466 which instructs the surgeon to replace digitizing tool 201 with paddle tool 204. Once replaced, the surgeon is then presented with an indicia 468 which instructs the surgeon to roughly place cutting guide 196.

After the rough placement of cutting guide 196, alignment guide 458 may be displayed. Alignment guide 458 displays a current varus/valgus and flex-extension angular offset 459 from a target origin, a current medial/lateral angular offset 463, and a current height offset 467. Further, alignment guide 458 provides instructions 461, 465, and 469 on how to adjust flex-extension angular offset 459, current medial/lateral angular offset 463, and current height offset 467, respectively. As the user adjusts cutting guide 196, flex-extension angular offset 459, current medial/lateral angular offset 463, and current height offset 467 are updated by processing system 110. In one embodiment, processing system 110 determines the desired cutting planes for resecting the bone and provides flex-extension angular offset 459, current medial/lateral angular offset 463, and current height offset 467 based thereon.

In one embodiment, input member 116 is a foot pedal. In one embodiment, processing system 110 provides step-by-step instructions for the surgical procedure (such as the screens in FIG. 43 and FIG. 44). The surgeon may move back and forth between these steps. In one embodiment, the surgeon is provided the opportunity to select which bone to cut first, such as either the tibia bone 210 or the femur bone 212 in a total knee replacement.

In one embodiment, instrumented linkage system 150 is coupled to femur bone 212 and is used to track the location of a surgical burr coupled to the free end of exemplary instrumented linkage system 150. Prior to cutting femur bone 212 with the surgical burr, the surgeon attaches digitizing tool 201 and digitizes a number of anatomical landmark points on femur bone 212. These landmark points enable processing system 110 to establish a reference coordinate system that is both affixed to femur bone 212 and able to recognize the spatial configuration of femur bone 212. The surgeon then replaces digitizing tool 201 with the surgical burr (which is coupled to the free end of instrumented linkage system 150) and proceeds to perform the bone cuts which are apart of the orthopedic operation.

During the cutting operation, processing system 110 tracks the location of the surgical burr and controls the cutting speed of the surgical burr based on the relative proximity of the cutting edge of the surgical burr to femur bone 212. Processing system 110 enables the surgeon to establish a pre-determined cutting enclosure for the surgical operation and delivers a pre-determined cutting speed at the surgical burr, the speed being dependent on the location of the cutting burr within the cutting enclosure. In one embodiment, the surgical burr includes a manual start/stop switch. In one embodiment, output member 118 displays real time images of the surgical burr and the target femur.

In one embodiment, instrumented linkage system 150 is coupled to femur bone 212 and is used to position a screw such that it will pass through a fixation plate of an intramedullary nail located within the femur. In one embodiment, instrumented linkage system 150 is coupled to one of femur bone 212 and tibia bone 210 and is used to position a drill.

Referring to FIGS. 30-33, another exemplary cutting guide 470 is shown. Cutting guide 470 includes a frame 472, a guide member 474, a sphere 476, and a retaining member 478. Guide member 474 includes three downward extending posts 480, 482, and 484 and a cutting guide slot 475. Post 480 is received in a channel 486 of frame 472 and then in channel 488 of sphere 476. Posts 482 and 484 are received in channels 490 and 492 of frame 472. Retaining member 478 keeps sphere 476 in contact with a spherical surface 494 of frame 472. Sphere 476 is retained relative to frame 472 by coupling retaining member 478 to frame 472.

In operation, cutting guide 470 is coupled to the bone, such as tibia bone 210. In one embodiment, cutting guide 470 is coupled by passing screws into apertures 496 of frame 472. The initial placement of cutting guide 470 may be a rough approximation of the final placement of a cutting guide slot 475 in guide member 474. In one embodiment, cutting guide 470 is roughly placed by coupling paddle tool 204 to instrumented linkage 100, placing paddle tool 204 in cutting guide slot 475, and locating cutting guide 470 in the approximate final location. In one embodiment, cutting guide 470 is roughly placed through operator judgment.

Once frame 472 is coupled to tibia bone 210, paddle tool 204 is coupled to instrumented linkage 100, 150 and inserted into cutting guide slot 475. Guide member 474 is moved to orient guide member 474 relative to frame 472. In one embodiment, channels 490 and channels 492 each include a double conical flare surface to permit the rocking of guide member 474 relative to frame 472. Once the angles are oriented correctly, grub screws are tightened in apertures 498 and into contact with sphere 476 to lock the orientation of sphere 476 relative to frame 472. At this point, guide member 474 may still be moved in direction 502 and direction 504 relative to frame 472 by grasping knob 500. Knob 500 is moved in direction 502 and direction 504, to obtain the correct height of cutting guide slot 475. Once the height is set correctly, grub screws are tightened in apertures 506 and into contact with downward extending posts 482 and posts 484.

Figure 38:
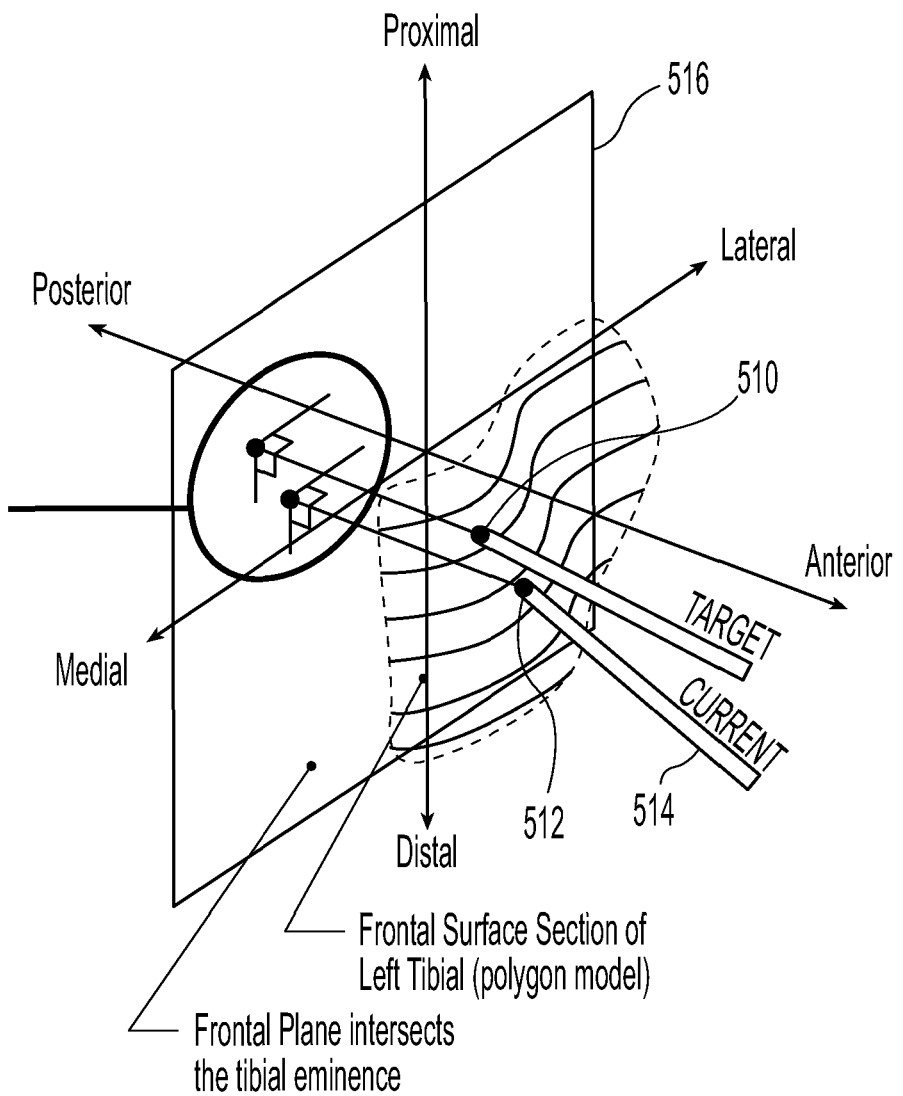
FIG. 38 is a representation of a current position of a tool tip and a target position of the tool tip.
Figure 39:
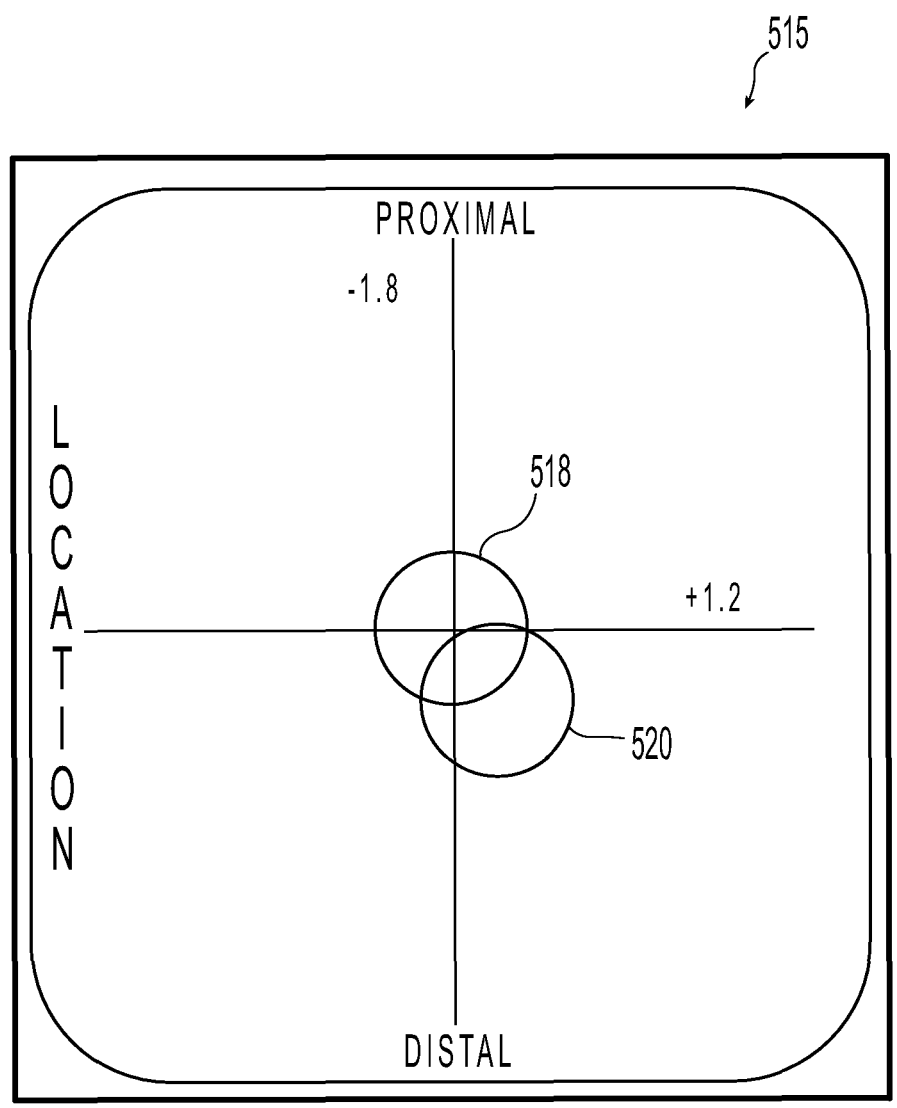
FIG. 39 is a screen display illustrating a misalignment of the current position of the tool tip from the target position.

In addition to assisting in the proper placement of a cutting guide, instrumented linkage 100 may be used to properly locate and orient a drill, other tool, or pin. Referring to FIG. 38, a target location 510 of a tool is shown along with a current location 512 of a tool 514. In one embodiment, processing system 110 projects locations 510 and 512 onto a plane 516 and to display a screen 515 (see FIG. 39) including both a representation 518 of target location 510 and a representation 520 of current location 512. By observing the relative locations of representation 518 and representation 520, an operator may move tool 514 to align representation 518 and representation 520. Another way in which the instrumented linkage 100 may be used is for Freehand Bone Cutting. In this case after digitizing the points, processing system 110 determines the required cutting plane in the bone. Instead of then attaching and aligning a slotted cutting guide to the bone, a small saw may be attached directly to the end of the instrumented linkage 100. The display then guides the surgeon to move the saw along the required cutting plane in the bone.

Figure 40:
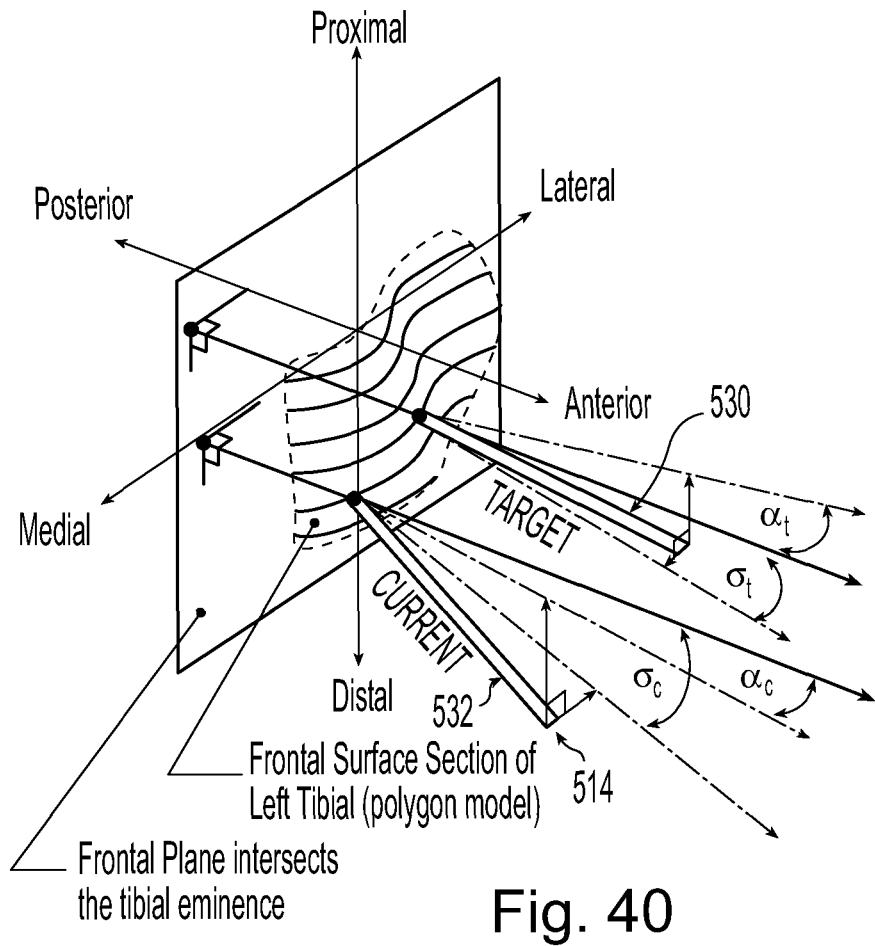
FIG. 40 is a representation of a current orientation of a tool and a target orientation of the tool.
Figure 41:
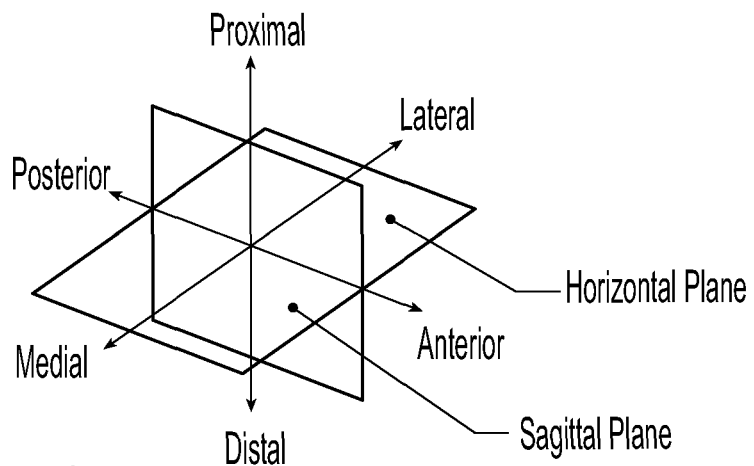
FIG. 41 is a representation of the coordinate planes of FIG. 40.

Referring to FIG. 40, a target orientation 530 of a tool is shown along with a current orientation 532 of a tool 514. In one embodiment, processing system 110 displays a screen 536 including both a representation 538 of target orientation 530 and a representation 540 of current orientation 532. Screen 536 also includes a representation 542 of a current orientation sagittal angle ($\sigma_{CO}$) and a representation 544 of a current orientation horizontal angle ($\alpha_{CO}$). The current orientation sagittal angle ($\sigma_{CO}$) being determined by:

current orientation sagittal angle ($\sigma_{CO}$)=sagittal target angle ($\sigma_t$)–sagittal current angle ($\sigma_c$).

The current orientation horizontal angle ($\alpha_{CO}$) being determined by:

current orientation horizontal angle ($\alpha_{CO}$)=horizontal target angle ($\alpha_t$)–horizontal current angle ($\alpha_c$).

Figure 42:
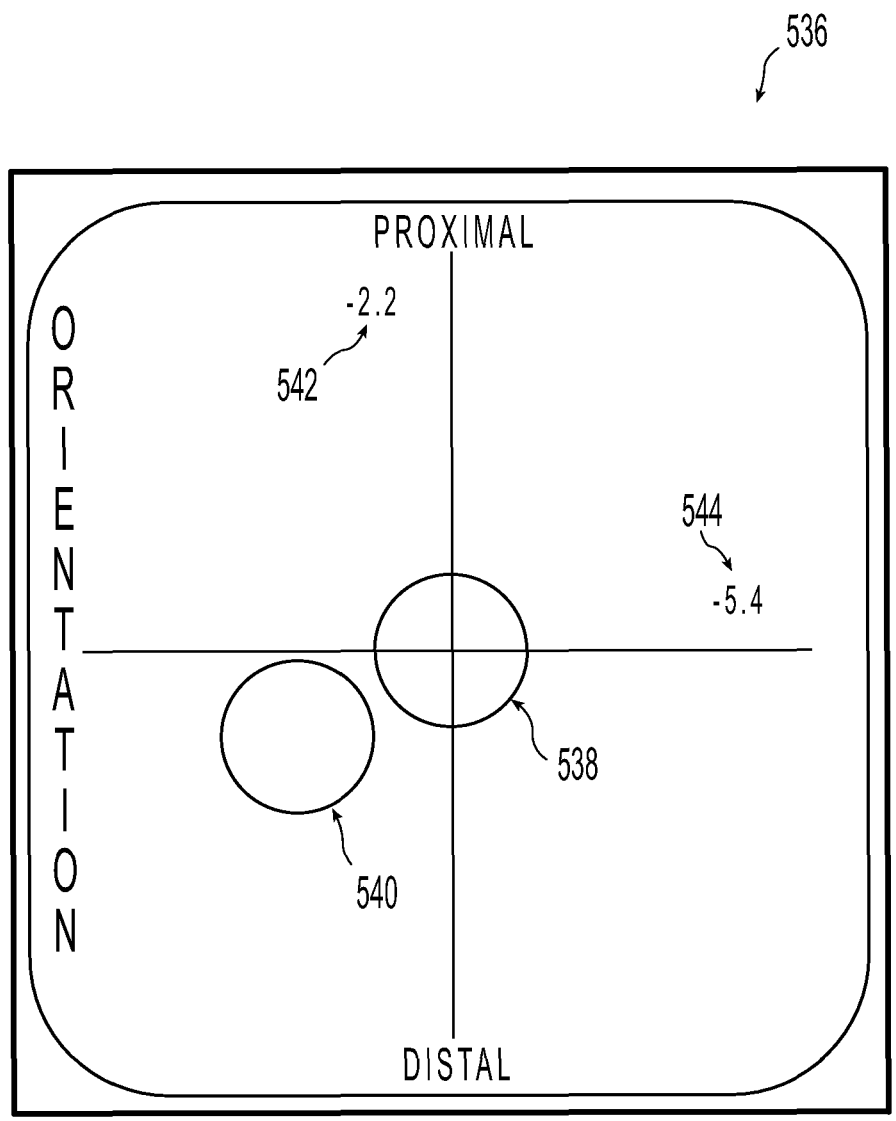
FIG. 42 is a screen display illustrating a misalignment of the current orientation of the tool and the target orientation of the tool.

By observing the relative locations of representation 518 and representation 520, an operator may move tool 514 to align representation 518 and representation 520. In one embodiment, an operator locates a contact point of a tool with interface screen 515 in FIG. 39 and then locates the proper orientation or direction of the tool with interface screen 536 in FIG. 42.

A second bone mount 188 may be coupled to the free end of exemplary instrumented linkage system 150. By having a first bone mount 188 attached to tibia bone 210 and a second bone mount 188 attached to femur bone 212, exemplary instrumented linkage system 150 may be used to determine femoral-tibial kinematics at ligament balancing and trial stages of a surgical procedure. Further, in this configuration exemplary instrumented linkage system 150 may be used to measure flexion angle of the joint.

Figure 45:
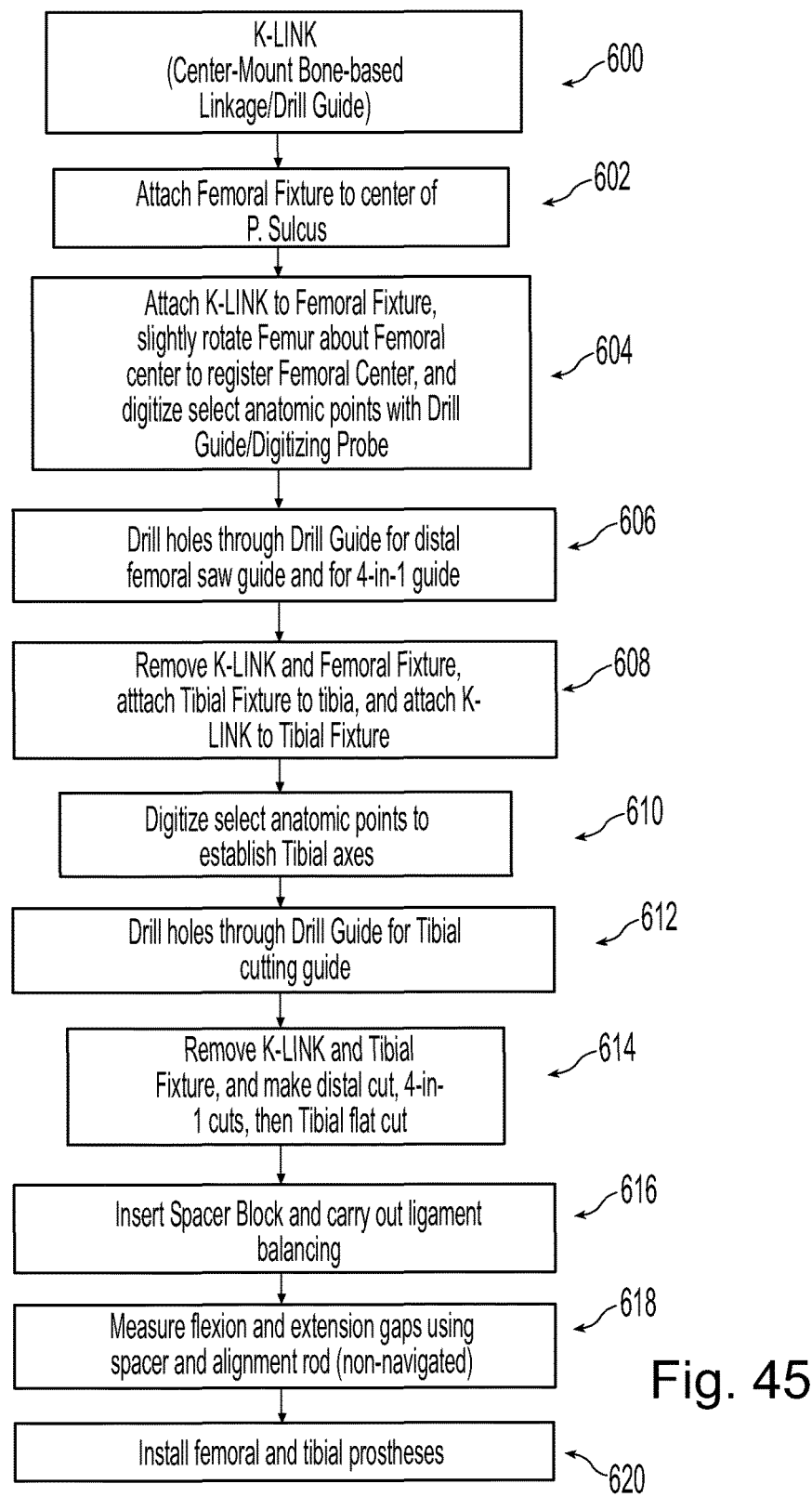
FIG. 45 is an exemplary method of a total knee replacement.
Figure 46:
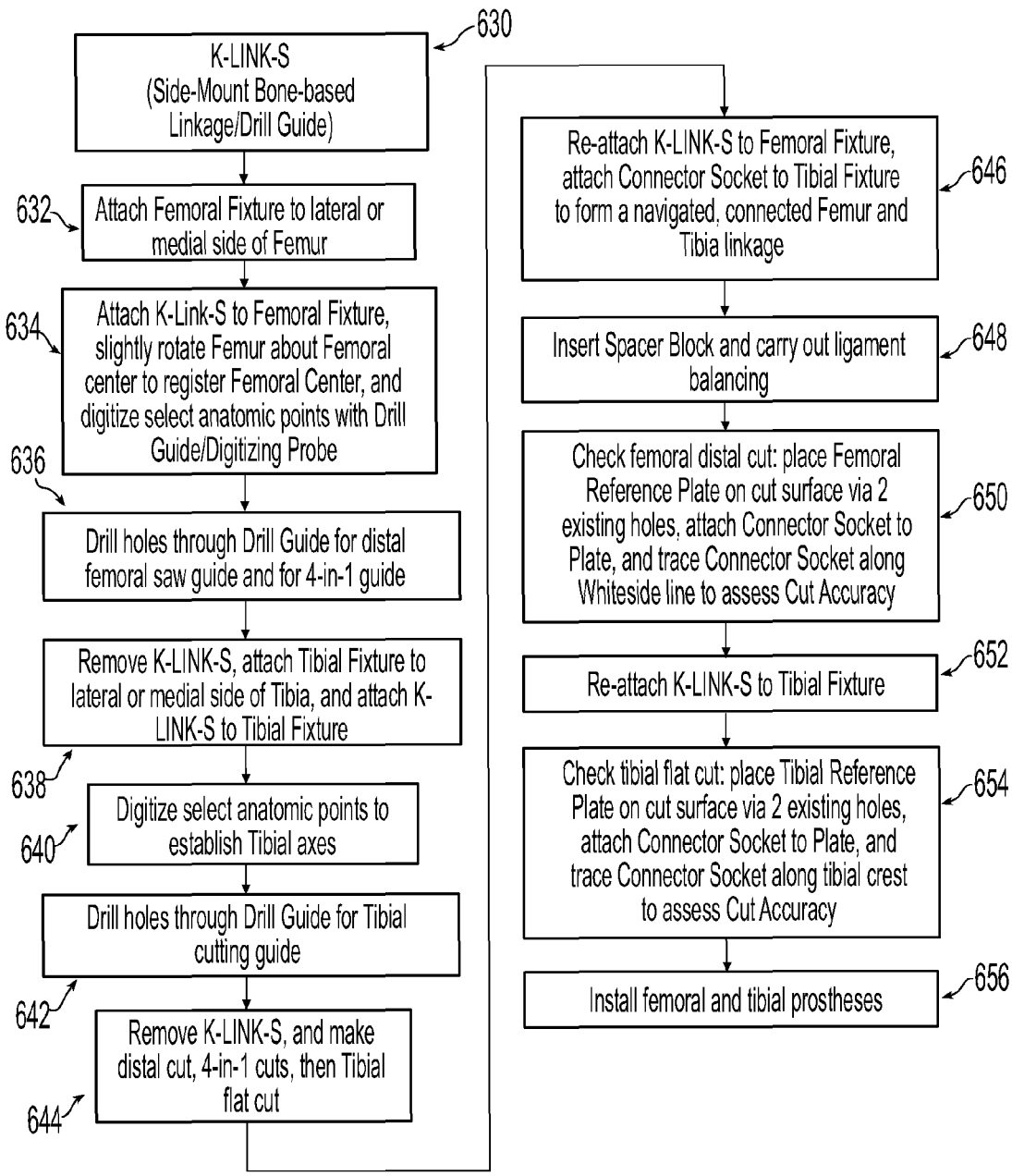
FIG. 46 is another exemplary method of a total knee replacement.

Referring to FIGS. 45 and 46, two exemplary methods of conducting a total knee replacement are shown. Each uses a type of instrumented linkage system attached to the bone. Exhibit B of U.S. Provisional Application Ser. No. 60/897,809, the disclosure of which is expressly incorporated by reference herein, includes a general description of these two methods along with two table mounted methods.

Turning to FIG. 45, a bone mounted instrumented linkage system, such as the ones described herein, is implemented, as represented by block 600. A fixture is attached to the center of P. Sulcus of the femur of the knee to be replaced, as represented by block 602. The fixture may be bone mount 188. The instrumented linkage system has a first end coupled to the fixture and a second end which is positioned at a known point on the patient support, as represented by block 604. The surgeon rotates the femur about the femoral center to register the femoral center, as represented by block 604. The surgeon then digitizes select landmark points on the femur with the instrumented linkage system, as represented by block 604. Exemplary landmark points include the proximate patella groove, the mid patella groove, the distal patella groove, the anterior cortex, the distal medial condyle, the distal lateral condyle, the posterior medial condyle, and the posterior lateral condyle. The instrumented linkage system is then used to provide the appropriate location and/or orientation to drill holes for a femoral saw guide and a 4-in-1 guide, as represented by block 606. An exemplary 4-in-1 guide is the 4-in-1 Femoral A/P Sizing and Rotation Guide available from Zimmer located at P.O. Box 708, 1800 West Center Street, Warsaw, Ind. 46581-0708. The femur fixture is removed and a tibia fixture is attached to the tibia bone of the knee to be replaced, as represented by block 608. The surgeon then digitizes select landmark points on the tibia with the instrumented linkage system, as represented by block 610. The instrumented linkage system is then used to provide the appropriate location and/or orientation to drill holes for a tibial cutting guide, as represented by block 612. The tibial fixture is removed and the various cuts are made in the femur and the tibia, as represented by block 614. A spacer block is inserted and a ligament balancing is carried out, as represented by block 616. The flexion and extension gaps are measured with a spacer and alignment rod, as represented by block 618. In one embodiment, the instrumented linkage system is coupled to both the femur and the tibia and is used to measure the flexion and extension gaps. The femoral and tibial prostheses are installed, as represented by block 620.

Turning to FIG. 46, a bone mounted instrumented linkage system, such as the ones described herein, is implemented, as represented by block 630. A fixture is attached to the lateral or medial side of the femur of the knee to be replaced, as represented by block 632. The fixture may be bone mount 188. The instrumented linkage system has a first end coupled to the fixture and a second end which is positioned at a known point on the patient support, as represented by block 634. The surgeon rotates the femur about the femoral center to register the femoral center, as represented by block 634. The surgeon then digitizes select landmark points on the femur with the instrumented linkage system, as represented by block 634. Exemplary landmark points include the proximate patella groove, the mid patella groove, the distal patella groove, the anterior cortex, the distal medial condyle, the distal lateral condyle, the posterior medial condyle, and the posterior lateral condyle. The instrumented linkage system is then used to provide the appropriate location and/or orientation to drill holes for a femoral saw guide and a 4-in-1 guide, as represented by block 636. An exemplary 4-in-1 guide is the 4-in-1 Femoral A/P Sizing and Rotation Guide available from Zimmer located at P.O. Box 708, 1800 West Center Street, Warsaw, Ind. 46581-0708. The instrumented linkage system is removed from the femur fixture and a tibia fixture is attached to the tibia bone of the knee to be replaced, as represented by block 638. The surgeon then digitizes select landmark points on the tibia with the instrumented linkage system, as represented by block 640. The instrumented linkage system is then used to provide the appropriate location and/or orientation to drill holes for a tibial cutting guide, as represented by block 642. The instrumented linkage system is removed from the tibial fixture and the various cuts are made in the femur and the tibia, as represented by block 644. The instrumented linkage system is reattached to both the femoral fixture and the tibial fixture, as represented by block 646. A spacer block is inserted and a ligament balancing is carried out with the instrumented linkage system, as represented by block 648. The femoral and tibial cuts are then checked with the instrumented linkage system, as represented by blocks 650, 652, and 654. The femoral and tibial prostheses are installed, as represented by block 656.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method of placing a cutting guide on at least one bone, the method comprising the steps of:

providing an instrumented linkage system having a first extremity and a second extremity, the first and second extremities interconnected and located on opposed ends of the instrumented linkage system;

affixing the first extremity of the instrumented linkage system to a substrate;

coupling a digitizing fixture to the second extremity of said instrumented linkage system;

digitizing a plurality of points of said at least one bone using the digitizing fixture;

coupling a cutting guide supporting fixture to said second extremity of said instrumented linkage system, said cutting guide supporting fixture having said cutting guide fixed thereto;

using the second extremity of the instrumented linkage system to locate said cutting guide, mounted to said second extremity of said instrumented linkage system, into a selected position relative to said at least one bone;

coupling a paddle fixture to the second extremity of said instrumented linkage system;

placing an end of said paddle fixture into a guide member of said cutting guide;

using the instrumented linkage system to adjusting an angular orientation of said paddle fixture to thereby adjust an angular orientation of said guide member relative to said at least one bone; and securing said cutting guide to said at least one bone.

2. The method of claim 1, wherein said substrate is a first bone.

3. The method of claim 2, wherein said step of affixing a first end of an instrumented linkage system to a substrate includes the steps of:

coupling a first member of a bone mount to said first bone with a fastener;
coupling a second member of said bone mount to said first member of said bone mount; and
coupling said second member of said bone mount to said instrumented linkage system.

4. The method of claim 1, wherein said substrate is a patient support and said step of affixing a first end of an instrumented linkage system to a substrate includes the steps of:
coupling a patient support mount to said substrate; and
coupling said instrumented linkage system to said patient support mount.

5. The method of claim 1, wherein said step of digitizing a plurality of points of said at least one bone includes the steps of:
prompting for a first landmark point;
receiving an indication that a tip of said digitizing fixture is positioned at said first landmark point; and
receiving an indication of a position of each of a plurality of moveable couplings of said instrumented linkage system.

6. The method of claim 1, wherein said step of locating said cutting guide includes the steps of:
affixing a frame of said cutting guide to said at least one bone; and
adjusting the angular orientation of said guide member relative to said frame based on a determined location of said end of said paddle fixture.

7. The method of claim 6, wherein said step of securing said cutting guide to said at least one bone further includes the steps of:
locking said angular orientation of said guide member relative to said frame;
adjusting a translational position of said guide member relative to said frame based on said determined location of said end of said paddle fixture; and
locking said translational position of said guide member relative to said frame.

* * * * *